United States Patent
Kaethner et al.

(10) Patent No.: US 11,423,539 B2
(45) Date of Patent: Aug. 23, 2022

(54) PROVISION OF A DIFFERENTIAL IMAGE DATASET AND A TRAINED GENERATOR FUNCTION

(71) Applicant: Siemens Healthcare GmbH, Erlangen (DE)

(72) Inventors: Christian Kaethner, Forchheim (DE); Sai Gokul Hariharan, Forchheim (DE); Markus Kowarschik, Nuremberg (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 194 days.

(21) Appl. No.: 16/891,446

(22) Filed: Jun. 3, 2020

(65) Prior Publication Data

US 2020/0394790 A1    Dec. 17, 2020

(30) Foreign Application Priority Data

Jun. 12, 2019 (DE) .......................... 102019208496.6

(51) Int. Cl.
*A61B 6/00* (2006.01)
*G06K 9/62* (2022.01)
*G06T 7/00* (2017.01)

(52) U.S. Cl.
CPC ............ *G06T 7/0012* (2013.01); *A61B 6/504* (2013.01); *G06K 9/6267* (2013.01); *G06T 2207/10116* (2013.01); *G06T 2207/20081* (2013.01); *G06T 2207/30101* (2013.01)

(58) Field of Classification Search
CPC ......... G06T 7/0012; G06T 2207/10116; G06T 2207/20081; G06T 2207/30101; G06T 2207/20084; G06T 2207/20224; G06T 7/0014; G06T 11/006; G06T 2211/404; A61B 6/504; A61B 6/481; G06K 9/6267; G06K 9/6256; G06V 10/30; G06V 10/82; G06V 2201/03; G06N 3/0454; G06N 3/084
See application file for complete search history.

(56) References Cited

U.S. PATENT DOCUMENTS

2019/0090834 A1    3/2019  Pauly
2019/0259492 A1*   8/2019  Reicher ................. G16H 30/20
(Continued)

OTHER PUBLICATIONS

Deuerling-Zheng Y. et al.: "Motion compensation in digital subtraction angiography using graphics hardware"; Computerized Medical Imaging and Graphics 30 (2006); pp. 279-289; 2006.
(Continued)

*Primary Examiner* — Siamak Harandi
(74) *Attorney, Agent, or Firm* — Harness, Dickey & Pierce, P.L.C.

(57) ABSTRACT

In an embodiment, a first real image dataset of an examination volume is received. The examination volume includes a vessel here, and the first real image dataset maps the examination volume includes contrast medium. Furthermore a differential image dataset of the examination volume is determined by application of a first trained generator function to input data. Here the input data includes the first real image dataset and a parameter of the trained generator function based on a GA algorithm. Furthermore the differential image dataset is provided.

20 Claims, 10 Drawing Sheets

(56) References Cited

U.S. PATENT DOCUMENTS

2020/0013153 A1    1/2020    Kaethner et al.
2020/0175328 A1*  6/2020    Bonakdar Sakhi .... G16H 50/50

OTHER PUBLICATIONS

Zhu et al., "Unpaired Image-to-Image Translation using Cycle-Consistent Adversarial Networks", 2017; pp. 2223-2232; 2017.
Bentoutou Y. et al.: "An invariant approach for image registration in digital subtraction angiography", in: Pattern Recognition, vol. 35, (2002), pp. 2853-2865.
Dabov, K. et. al.: "Video denoising by sparse 3d transform-domain collaborative filtering", in: Proc. 15th European Signal Processing Conference, 2007, pp. 145-149.
Image registration for DSA quality enhancement Thorsten M. Buzug, Jürgen Weese; Thorsten M. Buzug et al.; Image registration for DSA quality enhancement; Journal of Computerized Medical Imaging and Graphics; vol. 22, Issue 2, pp. 103-113 (Mar. 1998); 1998.
Costa, et al., "End-to-end adversarial retinal image synthesis." IEEE transactions on medical imaging, vol. 37, No. 3, Mar. 2018: pp. 781-791.; 2018.
Goodfellow, Ian J. et al.,"Generative Adversarial Networks", arXiv:1406.2661v1 of Jun. 10, 2014; XP055549980; pp. 1-9.
Wolterink et al., "Deep MR to CT synthesis using unpaired data", International Workshop on Simulation and Synthesis in Medical Imaging. Springer, Cham, 3. Aug. 2017.; 2017.
N. Taleb, Y. Bentoutou, O. Deforges, M. Taleb, "A 3D space-time motion evaluation for image registration in digital subtraction angiography", Comput Med Imag Graph 2001;25(3):223-33.; 2001.
Li, Y., Niu, K., Yang, P., Aagaard-Kienitz, B., Niemann, D.B., Ahmed, A.S., Strother, C. and Chen, G.H., 2016, March. Mask free Intravenous 3D Digital Subtraction Angiography (IV 3D-DSA) from a single C-arm acquisition. In Medical Imaging 2016: Physics of Medical Imaging (vol. 9783, p. 97830V). International Society for Optics and Photonics.; 2016.
Image Registration for Digital Subtraction Angiography; Meijering et al., International Journal of Computer Vision, 31 (2/3) 1999 pp. 227-246.
De Vos et al., "End-to-end unsupervised deformable image registration with a convolutional neural network", Deep Learning in Medical Image Analysis and Multimodal Learning for Clinical Decision Support. Springer, Cham, (2017); 2017.
Maggioni, M. et al.: "Video Denoising, Deblocking and Enhancement Through Separable 4-D Nonlocal Spatiotemporal Transforms", in: IEEE Trans. Image Process., 2012, vol. 21, No. 9, pp. 3952-3966.
M. Söderman, S. Holmin, T. Andersson, C. Palmgren, D. Babic, and B. Hoornaert, "Image noise reduction algorithm for digital subtraction angiography: Clinical results", Radiology, vol. 278, No. 3, pp. 962-962, 2016. / Originally published in: Radiology 2013;269(2):553-560 DOI: 10.1148/radiol.13121262; 2016.
M. Lebrun. "An analysis and implementation of the BM3D image denoising method", Image Processing on Line, 2 (2012), pp. 175-213, http://dx.doi.org/10.5201/ipol.2012.1-bm3d; 2012.
R. I. Ionasec, B. Heigl, J. Hornegger, "Acquisition-related motion compensation for digital subtraction angiography", Computerized medical imaging and graphics 33.4 (2009): 256-266.; 2009.
Hariharan et al.,2018. Simulation of Realistic Low Dose Fluoroscopic Images from their High Dose Counterparts. In Bildverarbeitung fur die Medizin 2018 (pp. 80-85). Springer Vieweg, Berlin, Heidelberg.; 2018.
Niu, Kai et al.: "Ultra low radiation dose digital subtraction angiography (DSA) imaging using low rank constraint"; in: Proceedings of the SPIE—Physics of Medical Imaging; vol. 94121O; 2015; DOI: 10.1117/12.2082070.
Jaderberg, Max, et al., "Spatial Transformer Networks", arXiv:1506.02025v3 of Feb. 4, 2016.
Wikipedia "Generative Adversarial Networks" https://de.wikipedia.org/w/index.php?title=Generative_Adversaria!_Networks&oldid=186990065 (Mar. 27, 2019) // https://en.wikipedia.org/wiki/Generative_adversarial_network (Aug. 18, 2020).
Nie, Dong et al. "Medical Image Synthesis with Context-Aware Generative Adversarial Networks" arXiv:1612.05362v1 [cs.CV] Dec. 16, 2016.
Montoya, Juan C. et al. "3D Deep Learning Angiography (3D-DLA) from C-arm Conebeam CT" American Journal of Neuroradiology, vol. 38, No. 5, pp. 916-922, 2018.
Goodfellow, Ian J. et al. "Generative Adversarial Nets" NIPS'14 Proceedings of the 27th International Conference on Neural Information Processing Systems—vol. 2, pp. 2672-2680, Montreal, Canada—Dec. 8-13, 2014 (arXiv:1406.2661v1).
Wolterink, Jelmer M. et al. "Generative adversarial networks for noise reduction in low-dose CT" IEEE transactions on medical imaging, 36, No. 12, pp. 2536-2545, Dec. 2017.
German Office Action dated Jun. 8, 2020.
Hao, H.: "Vessel Layer Separation of X-ray Angiographic Images using Deep Learning Methods"; Master Thesis, retrieved Online: https://repository.tudelf.nl/islandora/object/uuid%3Aae819077-c7cd-4737-ad6e-7289cb39e3bd; 2018;.
Armaniuos, K. et al.: Unsupervised Medical Image Translation Using Cycle-MedGAN; Preprint 1903.03374v1 auf arXiv.org; 2019;.
Unberath, M. et al.: "Deep Learning-based Inpainting for Virtual DSA"; Online: https://www.researchgate.net/publication/321251358_Deep_Learning-based_Inpainting_for_Virtual_DSA; 2017;.

\* cited by examiner

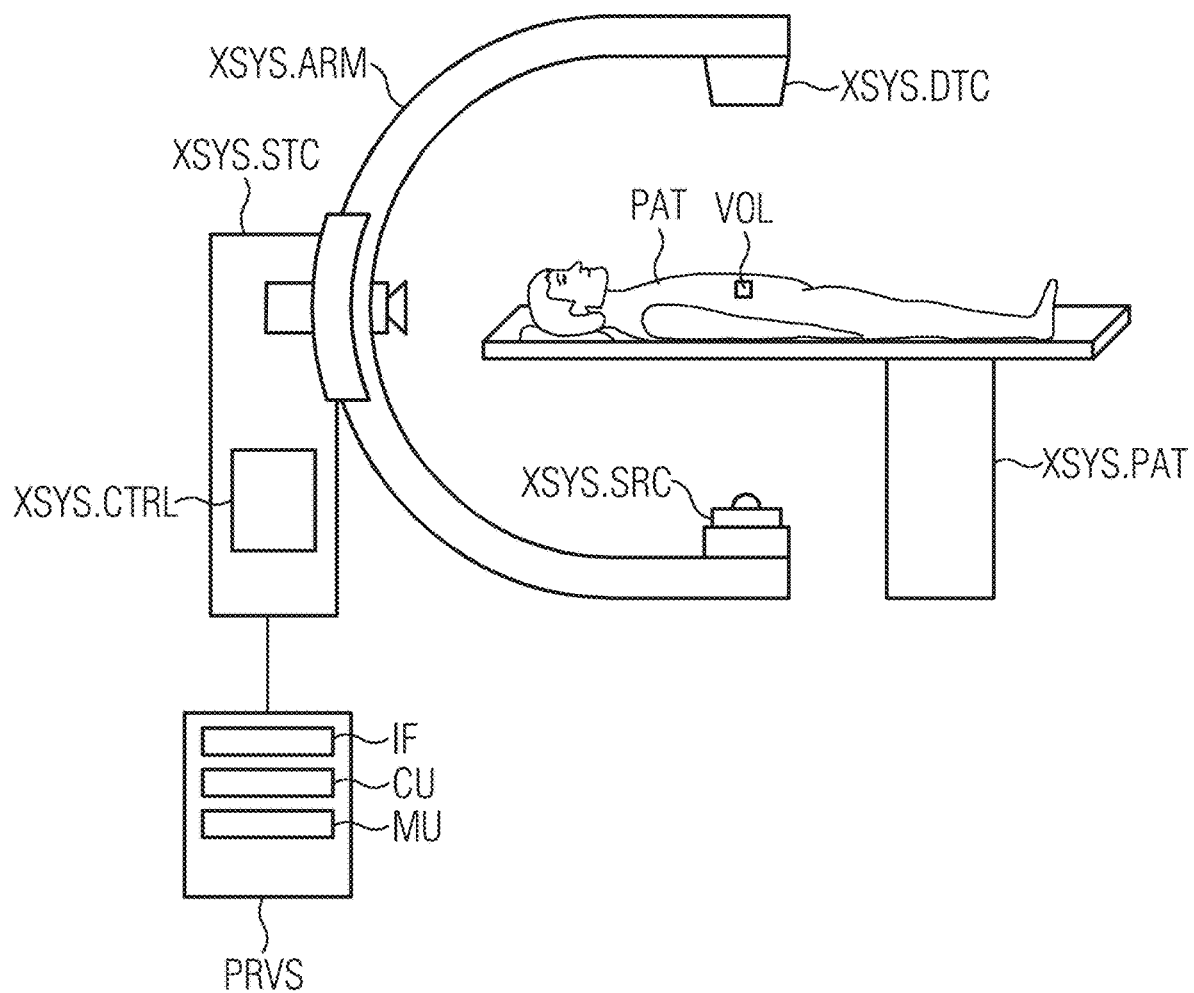

PROVISION OF A DIFFERENTIAL IMAGE DATASET AND A TRAINED GENERATOR FUNCTION

PRIORITY STATEMENT

The present application hereby claims priority under 35 U.S.C. § 119 to German patent application number DE 102019208496.6 filed Jun. 12, 2019, the entire contents of which are hereby incorporated herein by reference.

FIELD

Embodiments of the invention generally relate to provisioning of a differential image dataset and/or a trained generator function.

BACKGROUND

X-ray facilities are often employed in medical practice for monitoring of (in particular minimally invasive) surgical interventions; in some cases specific interventions are only possible through x-ray monitoring, for example the implantation of an aortic valve via a catheter.

The advantages of such an x-ray monitored intervention must be weighed here against the radiation load caused by the dose of x-ray radiation absorbed. Since typically the reduction of the x-ray dose is also accompanied by a reduction in the image quality or by an increase in the signal-to-noise ratio, a compromise must frequently be found between good image quality and low x-ray dose.

If the signal-to-noise ratio is too high, this can also lead in particular to a low image quality in digital subtraction angiography (abbreviated to DSA). In particular the necessary registration of mask image dataset and x-ray image dataset may not be possible, or the noise may lead to artifacts in the registration.

In digital subtraction angiography (abbreviated to DSA) one or more vessels in an examination volume are represented by x-ray images, wherein, for the suppression of further structures in the examination volume, images of the vessel without contrast medium (known as mask images) are combined with images of the vessel including a contrast medium that is located in the vessel. The contrast medium is introduced here into the vessel during the examination, in order to determine parameters, in particular hydrodynamic parameters of a fluid, wherein the fluid is flowing in the vessel.

For a digital subtraction angiography, the fact that both images of the vessel without contrast medium and also images of the vessel including a contrast medium are recorded means that the examination volume is subjected to a higher x-ray load. The images of the vessel without contrast medium are also referred to as mask images.

A known practice is to increase the image quality by various noise suppression methods. However these methods can change the impression of the image and/or can lead to artifacts. If noise suppression is applied to too high a degree, this can lead to an cartoon-like impression of the image for example.

Furthermore optimization of the signal-to-noise ratio by optimized protocols (i.e. through an optimized choice of the parameters of the x-ray facility) is known. However this choice of protocols can also change the impression of the image (for example the values of the image pixels can differ for the same imaged structure at different image recording values). This represents a problem in particular if the image data is to be further processed by trained algorithms, in particular if the algorithms used for training have only been recorded via a restricted number of protocols or a restricted number of x-ray facilities.

The determination of a differential image dataset by applying a trained function to a real image dataset without recording an additional mask image is known from the unpublished patent application EP18182251. Here however the noise level of the differential image dataset corresponds to the noise level of the real dataset. Therefore, although a mask recording can be dispensed with, a real image dataset with a low noise level and thus a high x-ray dose must be used for a reduction of the noise level in the differential image dataset.

SUMMARY

At least one embodiment of the invention therefore provides a differential image dataset with a low noise level, based on a real image dataset.

Embodiments of the invention are directed to a computer-implemented method for provision of a differential image dataset; a computer-implemented method for provision of a trained generator function; a provision system; an x-ray facility; a computer program product; and a computer-readable storage medium. Advantageous developments are described in the claims and in the description given below.

The inventive aspects are described below both in relation to the claimed facilities and also in relation to the claimed method. Features, advantages or alternate forms of embodiment mentioned here are likewise to be transferred to the other claimed subject matter and vice versa. In other words the physical claims (which are directed to a facility for example) can also be further developed with the features that are described or claimed in conjunction with a method. The corresponding functional features of the method are embodied in such cases by corresponding physical modules.

Furthermore the inventive aspects are described below both in relation to the method and facilities for provision of differential images and also in relation to the method and facilities for provision of trained generator functions. Features and alternate forms of embodiment of data structures and/or functions in methods and facilities for provision of differential images can be transferred here to similar data structures and/or functions in methods and facilities for provision of trained generator functions. Similar data structures can be identified here in particular in that they are preceded by the term "training". Furthermore the trained generator functions used in methods and facilities for the provision of differential images may have been adapted and/or provided by methods and facilities for provision of trained generator functions.

In a first embodiment, the invention relates to a computer-implemented method for provision of a differential image dataset. The method is based on a first real image dataset of an examination volume being received, in particular via an interface. Here the examination volume comprises a vessel and the first real image dataset maps the examination volume including contrast medium. Furthermore a differential image dataset of the examination volume is determined by application of a first trained generator function to input data, in particular via a computing unit. Here the input data comprises the first real image dataset and a parameter of the trained generator function based on a GA algorithm. Furthermore the differential image dataset is provided, in particular via the interface.

In a second embodiment the invention relates to a computer-implemented method for provision of a first trained generator function. The method is based on a real image dataset and a comparison differential image dataset of the examination volume being received, in particular via a training interface. Furthermore a differential image dataset of the examination volume is determined by application of a first trained generator function to first input data, the first input data comprising the real image dataset here. Furthermore a first classification value is determined by application of a first trained classifier function to the differential image dataset, and a second classification value is determined by application of the first trained classifier function to the comparison differential image dataset, in particular via a training computing unit. Furthermore there is an adaptation of the first trained generator function and/or the first trained classifier function based on the first classification value and/or the second classification value, in particular likewise via the trainings computing unit. Furthermore there is a provision of the trained generator function, in particular via the training interface. The provision of the trained generator function can in particular comprise storage, transfer and/or display of the trained generator function.

In a third embodiment the invention relates to a provision system for provision of a differential image dataset of an examination volume, comprising an interface and a computing unit,
wherein the interface is embodied to receive a first real image dataset of the examination volume,
wherein the examination volume comprises a vessel,
wherein the first real image dataset comprising the examination volume maps contrast medium,
wherein the computing unit is embodied to determine the differential image dataset of the examination volume by application of a first trained generator function to input data,
wherein the input data comprises the first real image dataset,
wherein a parameter of the first trained generator function is based on a GA algorithm,
wherein the interface is furthermore embodied for provision of the differential image dataset.

In a possible fourth embodiment the invention relates to an x-ray facility, comprising an x-ray source and an x-ray detector, furthermore comprising a provision system according to the third embodiment of the invention. An x-ray facility can in particular involve a C-arm x-ray facility or a computed tomography unit.

In a possible fifth embodiment the invention relates to a training system for provision of a first trained generator function, comprising a training interface and a training computing unit,
wherein the training interface is embodied to receive a first real image dataset of an examination volume,
wherein the training interface is furthermore embodied to receive a comparison differential image dataset of the examination volume,
wherein the computing unit is embodied to determine a differential image dataset of the examination volume by application of a first trained generator function to first input data,
wherein the first input data comprises the first real image dataset,
wherein the computing unit is furthermore embodied to determine a first classification value by application of a first trained classifier function to the differential image dataset,
wherein the computing unit is furthermore embodied to determine a second classification value by application of the first trained classifier function to the comparison differential image dataset,
wherein the computing unit is furthermore embodied to adapt the first trained generator function and/or the first trained classifier function based on the first classification value and/or the second classification value,
wherein the training interface is furthermore embodied for provision (PRV-GF-1) of the first trained generator function (GF-1).

Such a training system can in particular be embodied to carry out the inventive methods for provision of a first trained generator function and their embodiments described above. The training system is embodied to carry out these methods and their embodiments, in that the interface and the computing unit are embodied to carry out the corresponding method steps.

In a sixth embodiment the invention relates to a computer program product with a computer program, which is able to be loaded directly into a memory of a provision system, with program sections for carrying out all steps of the method for provision of a differential image dataset and its embodiments when the program sections are executed by the provision system; and/or which is able to be loaded directly into a memory of a training system, with program sections for carrying out all steps of the method for provision of a differential image dataset and its embodiments when the program sections are executed by the training system.

In particular, an embodiment of the invention relates to a computer program product with a computer program, which is able to be loaded directly into a memory of a provision system, with program sections for carrying out all steps of the method for provision of a differential image dataset and its embodiments when the program sections are executed by the provision system.

In particular, an embodiment of the invention relates to a computer program product with a computer program, which is able to be loaded directly into a training memory of a training system, with program sections for carrying out all steps of the method for provision of a first trained generator function and its embodiments when the program sections are executed by the training system.

In a seventh embodiment the invention relates to a computer-readable storage medium, on which program sections able to be read and executed by a provision system are stored, in order to carry out all steps of the method for provision of a differential image dataset and its embodiments when the program sections are executed by the provision system; and/or on which program sections able to be read and executed by a training system are stored, in order to carry out all steps of the method for provision of a first trained generator function and its embodiments when the program sections are executed by the training system.

In particular, an embodiment of the invention relates to a computer-readable storage medium, on which program sections able to be read and executed by a provision system are stored, in order to carry out all steps of the method for provision of a first trained generator function and its embodiments when the program sections are executed by the provision system.

In particular, an embodiment of the invention relates to a computer-readable storage medium, on which program sections able to be read and executed by a training system are stored, in order to carry out all steps of the method for provision of a first trained generator function and its embodiments when the program sections are executed by the training system.

In an eighth embodiment the invention relates to a computer program or a computer-readable storage medium, comprising a first trained generator function, provided by a method for provision of a first trained generator function.

At least one embodiment of the invention is directed to a computer-implemented method for provision of a differential image dataset of an examination volume, comprising:

receiving a first real image dataset of the examination volume, the examination volume including a vessel, the first real image dataset mapping the examination volume including contrast medium;

determining the differential image dataset of the examination volume by application of a first trained generator function to input data, the input data including the first real image dataset received, a parameter of the first trained generator function being based on a GA algorithm; and provisioning the differential image dataset determined.

At least one embodiment of the invention is directed to a computer-implemented method for provision of a first trained generator function, comprising:

receiving a first real image dataset of an examination volume;

receiving a comparison differential image dataset of the examination volume;

determining a differential image dataset of the examination volume by application of a first trained generator function to first input data, the first input data including the first real image dataset received;

determining a first classification value by application of a first trained classifier function to the differential image dataset determined;

determining a second classification value by application of the first trained classifier function determined to the comparison differential dataset received;

adapting at least one of the first trained generator function and the first trained classifier function based on at least one of the first classification value and the second classification value; and provisioning the first trained generator function.

At least one embodiment of the invention is directed to a computer-implemented method for provision of a differential image dataset of an examination volume, comprising:

receiving a first real image dataset of the examination volume, the examination volume including a vessel, the first real image dataset mapping the examination volume including contrast medium;

determining the differential image dataset of the examination volume by application of a first trained generator function to input data, the input data including the first real image dataset received, a parameter of the first trained generator function being based on a GA algorithm; and provisioning the differential image dataset determined, wherein the first trained generator function has been provided by the method of claim 10.

At least one embodiment of the invention is directed to a provision system for provision of a differential image dataset of an examination volume, comprising:

an interface embodied to receive of a first real image dataset of the examination volume, the examination volume including a vessel and the first real image dataset mapping the examination volume including contrast medium; and a computing unit, embodied to determine the differential image dataset of the examination volume by application of a first trained generator function to input data, the input data including the first real image dataset and a parameter of the first trained generator function being based on a GA algorithm, wherein the interface is further embodied to provision the differential image dataset.

At least one embodiment of the invention is directed to a non-transitory computer program product storing a computer program, directly loadable into a memory unit of a provision system or training system, including program sections for carrying out the method of an embodiment when the program sections are executed by the provision system or training system.

At least one embodiment of the invention is directed to a non-transitory computer-readable storage medium storing program sections, readable and executable by a provision system or training system, for carrying out the method of an embodiment when the program sections are executed by the provision system or training system.

BRIEF DESCRIPTION OF THE DRAWINGS

The characteristics, features and advantages of this invention described above, as well as the manner in which these are achieved, will become clearer and easier to understand in conjunction with the description given below of the example embodiments, which are explained in greater detail in conjunction with the drawings. This description does not impose any restriction of the invention to these example embodiments. In different figures the same components are provided with identical reference characters. As a rule the figures are not true-to-scale. In the figures:

FIG. 13 shows an x-ray facility.

DETAILED DESCRIPTION OF THE EXAMPLE EMBODIMENTS

Figure 1:
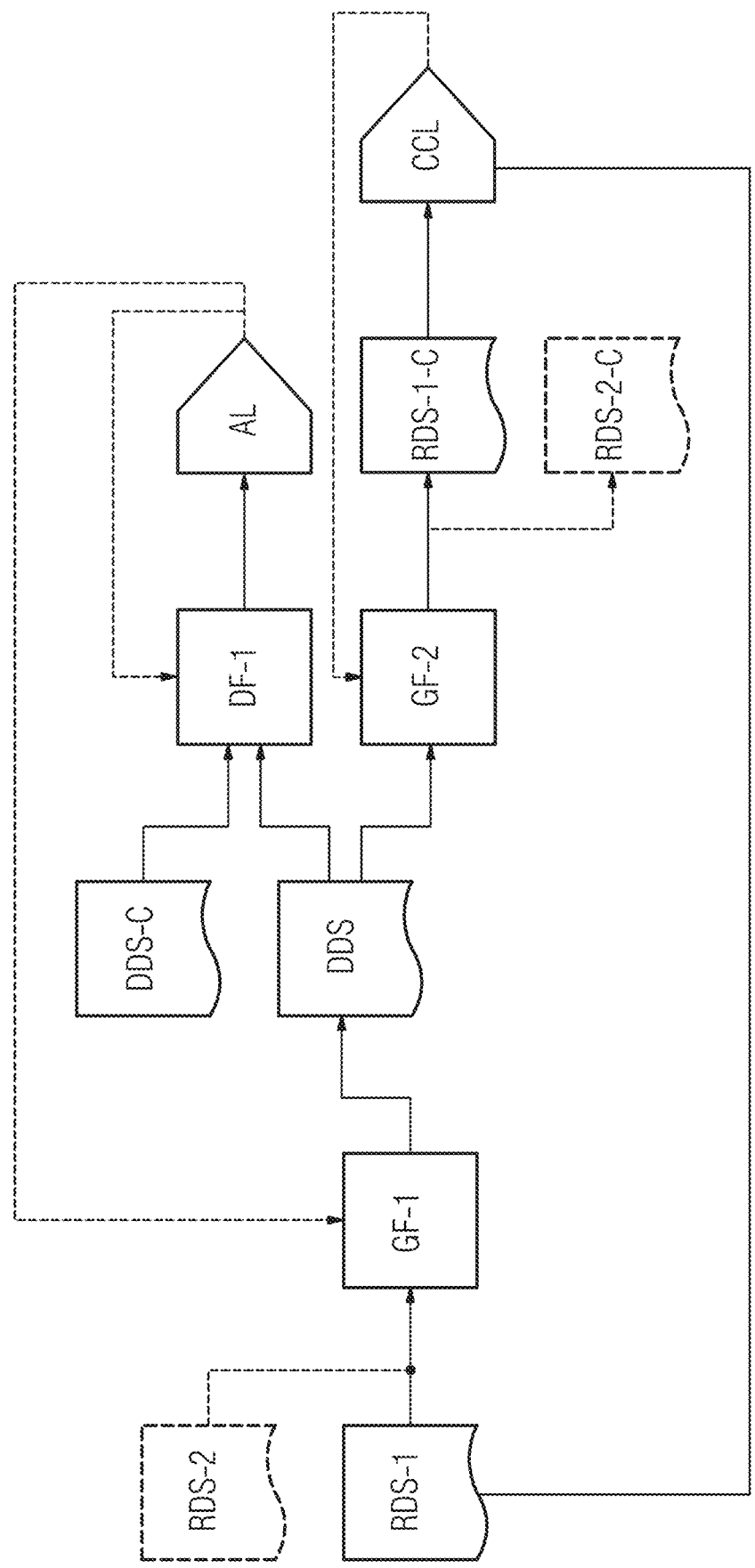
FIG. 1 shows a first data flow diagram of the method in accordance with the invention and its embodiments.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central At least one processor (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central At least one processor (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer at least one processors into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewritable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewritable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules.

References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewritable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewritable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In a first embodiment, the invention relates to a computer-implemented method for provision of a differential image dataset. The method is based on a first real image dataset of an examination volume being received, in particular via an interface. Here the examination volume comprises a vessel and the first real image dataset maps the examination volume including contrast medium. Furthermore a differential image dataset of the examination volume is determined by application of a first trained generator function to input data, in particular via a computing unit. Here the input data comprises the first real image dataset and a parameter of the trained generator function based on a GA algorithm. Furthermore the differential image dataset is provided, in particular via the interface.

An image dataset in particular comprises a plurality of pixels or voxels. In such cases each pixel or voxel is assigned an intensity value. An image dataset can in particular be an x-ray image dataset. In an x-ray image dataset in particular each pixel or voxel is an x-ray intensity value, which is a measure for the incident x-ray intensity in this pixel or voxel or for an x-ray absorption coefficient of the pixel or of the voxel. An incident x-ray intensity depends on the number, the size, the form and the material of the objects located in the examination volume and penetrated by the x-ray radiation. An image dataset can in particular comprise further data, in particular metadata of an imaging examination, in particular of an x-ray examination.

A two-dimensional image dataset in this case comprises at least one two-dimensional representation of an examination volume. A three-dimensional image dataset in this case comprises at least one three-dimensional representation of an examination volume, in particular a three-dimensional image dataset can also additionally also comprise one or more two-dimensional representations of the examination volume. A three-dimensional representation can in particular be spatially three-dimensional, a three-dimensional representation can however also be spatially two-dimensional and temporally one-dimensional. A four-dimensional image dataset in this case comprises at least one four-dimensional representation of an examination volume. A four-dimensional representation of the examination volume can in particular be spatially three-dimensional and temporally one-dimensional.

An image dataset can be referred to in particular as a real image dataset if it maps the actual distribution of values and/or intensities (e.g. Hounsfield units, coefficients of x-ray attenuation) in an examination volume. An image dataset can in particular be referred to as a differential image dataset if it maps a difference between an actual distribution of values and/or intensities in an examination volume. A differential image dataset is not necessarily determined by subtraction of two real image datasets. An image dataset can in particular be referred to as a subtraction image dataset if it was determined by subtraction of two image datasets, in particular by subtraction of two real image datasets. Therefore each subtraction image dataset can be expressed in a differential image dataset, but not every differential image dataset can be expressed as a subtraction image dataset.

A trained function is in particular a function that maps input data to output data, wherein the output data furthermore depends on at least one function parameter of the function, and wherein the function parameter is able to be adapted by supervised learning, by semi-supervised learning and/or by unsupervised learning. The input data and/or the output data here can in particular each comprise at least one image dataset.

In particular a trained generator function is a trained function, and a trained classifier function is a trained function. With a trained function one of its parameters does not necessarily have to have been already adapted, therefore the term trained function can also be replaced by trainable function, in particular the term trained generator function can be replaced by trainable generator function and/or the term trained classifier function by trainable classifier function. In particular the terms trained generator function and generator function can be used as synonyms, and/or the terms trained classifier function and classifier function can be used as synonyms.

In a trained generator function the input data and the output data in particular comprise at least one image dataset. In a trained classifier function the input data in particular comprises at least one image dataset, and the outputs comprise one or more probability values. The probability value corresponds in particular to the probability of the image dataset of the input data being a real image dataset or a synthetic image dataset. The designation "classifier function" can in particular be replaced by the designation "discriminator function" and/or by the designation "discriminator and classifier function" or by the designation "classifier and discriminator function".

A GA algorithm (GA is an acronym for generative adversarial) comprises a generator function and a classifier function. Here the generator function creates synthetic data (another term is virtual data), and the classifier function differentiates between synthetic and real data. In particular what is achieved by training the generator function and/or the classifier function is that on the one hand the generator function creates synthetic data of the type that is incorrectly classified as real by the classifier function, on the other hand the classifier function can distinguish as well as possible between real data and synthetic data. In game theory a GA algorithm can also be expressed as a zero-sum game. The training of the generator function and/or of the classifier function is based in particular on the minimization of a loss function in each case.

If the generator function and the classifier function are provided by a network, in particular by an artificial neural network, then the GA algorithm can also be referred to as a GA network (also GAN for generative adversarial network). These are known in particular from the publication by Ian J. Goodfellow, "Generative Adversarial Networks", arxiv 1406.2661 (2014), the entire contents of which are hereby incorporated herein by reference. The minimization of the loss function can take place in particular via a gradient descent, and in particular via backpropagation.

A parameter of the trained generator function is based in particular on a GA algorithm or on a GA network in such a way that the parameter of the trained generator function is identical to a parameter of the generator function of the GA algorithm or of the GA network. In particular a parameter of the trained generator function is based on a GA algorithm or on a GA network in such a way that the trained generator function is identical to the generator function of the GA algorithm or of the GA network.

The inventors have recognized that, through the method described, a differential image dataset of an examination volume can be established based on a real image dataset of the examination volume, wherein through the use of a trained generator function the differential image dataset can have different characteristics from the real image dataset. In particular the method described can be employed to reduce the noise in image datasets. This for example enables the x-ray dose used or the amount of contrast medium used to be reduced in x-ray imaging, wherein at the same time the quality of the differential image dataset can be kept at least constant.

According to a further embodiment of the invention the first real image dataset has a first noise level, and the differential image dataset has a second noise level. The first noise level is higher than the second noise level here.

The noise level of an image dataset relates in particular to the intensity of the noise in the image dataset. Advantageously the noise level can be described by the signal-to-noise ratio (wherein the noise level rises when the signal-to-noise ratio falls, and wherein the noise level falls when the signal-to-noise ratio rises). Usually in x-ray imaging the signal-to-noise ratio rises with the x-ray dose used.

The inventors have recognized that, through this choice of noise level, differential image datasets can be created that have a lower noise level than the first real image datasets used as input data. This enables a lower x-ray dose to be used in the recording of the real image datasets than would be necessary for direct recording of an image dataset with the desired second noise level.

The trained generator function can in particular effect this reduction of the noise level, if in the GA training or in the GA algorithm it is applied to real image datasets with a first training noise level, and the result of the training is compared with differential images having a second training noise level (in particular via a trained classifier function), wherein the second training noise level is lower than the first training noise level.

According to a further embodiment of the invention the first real image dataset is an x-ray image dataset, in particular a two-dimensional or three-dimensional x-ray image dataset.

The inventors have recognized that, by applying the method to x-ray image datasets, the noise level of the differential image dataset can be lowered, without at the same time increasing the x-ray dose and thus the radiation load on the examination volume.

According to a further embodiment of the invention the method for provision of a differential image dataset furthermore comprises a determination of a mask image dataset of the examination volume by applying the first trained generator function to the input data, wherein the mask image dataset maps the examination volume without contrast medium. The determination takes place in particular via the computing unit. In particular the first trained generator function can only be applied once to the input data, and the result of the application of the first trained generator function comprises the mask image dataset and the differential image dataset.

The inventors have recognized that, through the additional generation of a mask image dataset of the examination volume as well as the differential image dataset, a plausibility check can be carried out, in that the differential image dataset can be compared with the difference of the first real image dataset and the mask image dataset. In particular, with a strong deviation, it can be established that the received first real image dataset deviates too much from the image datasets used in training the first trained generator function, and therefore the result of the application of the first trained generator function of the differential image dataset cannot be used reliably.

According to a further possible embodiment of the invention the method for provision of a differential image dataset furthermore comprises the receipt of a mask image dataset of the examination volume. Here the mask image dataset maps the examination volume without contrast medium, and the input data of the trained generator function comprises the mask image dataset.

In particular the mask image dataset can have a third noise level, which is higher than the second noise level of the differential image dataset. In particular the third noise level and the first noise level of the first real image dataset can be similar or identical.

The inventors have recognized that through the use of a mask image dataset in the input data the first trained generator function has further information available to it about the structure of the examination volume, which can be used in the determination of the differential image dataset. In particular, through the use of a mask image dataset, it does not have to be decided solely on the basis of intensity values of the first real image dataset whether a pixel or a voxel of the first real image dataset is to be assigned to a vessel or to the background.

According to a further embodiment of the invention the method for provision of the differential image dataset furthermore comprises a receipt of a second real image dataset of the examination volume. Here the first real image dataset maps the examination volume at a first point in time, and the second real image dataset maps the examination volume at a second point in time. Furthermore the input data of the trained generator function here comprises the second real image dataset.

The first and the second real image dataset can in particular be two-dimensional image datasets here, which have been recorded during one rotation of a C-Arm x-ray facility about the examination volume. In particular the first and the second real image dataset can have been recorded in order to carry out a three-dimensional reconstruction of the examination volume.

The inventors have recognized that through the use of a second real image dataset, which was recorded at a different point in time to the first real image dataset, the application of the trained generator function can be based on more information of the examination volume. In particular better account can be taken of the noise through this, assuming that the noise in the first real image dataset and in the second real image dataset is statistically independent.

According to a further embodiment of the invention the first trained generator function is applied in sections to the image datasets contained in the input data. In particular the image datasets contained in the input data are divided here into a number of part image datasets, and the first trained generator function is applied to each of the number of part image datasets. The individual part results are then in particular assembled into a result again. The individual part image datasets can advantageously be disjoint, but it is also possible for the individual part image datasets to overlap.

The inventors have recognized that through the section-by-section application of the first trained generator function, although said function can be applied multiple times, each of the applications relates to fewer pixels or voxels however. Since the characteristics of the individual sections correspond to the characteristics of the overall image datasets, training of the trained generator function will be made easier, since on the one hand the trained generator function can comprise fewer parameters, and on the other hand there is more training data available (since the training data can also be divided into a number of items of part training data). Through this the application of the trained generator function is more precise or the training of the trained generator function requires less effort.

According to a further embodiment of the invention the parameter of the first trained generator function is based on a cyclic consistency loss function.

A parameter of a trained function is based in particular on a loss function if the parameter for minimization or maximization of this loss function has been adapted or changed.

A cyclic consistency loss function is in particular a loss function based on a comparison of a double application of the trained generator function with the input data. In particular the cyclic consistency loss function is based on a norm of the difference of the input image dataset and the application of the trained generator function to input data comprising the result image dataset and the input image parameter. The norm can in particular involve a 1-norm or a 2-norm, the norm can in particular be evaluated pixel-by-pixel or voxel-by-voxel.

What can be achieved through the use of a cyclic consistency loss function is that a multiple application of trained generator functions (in this case one application of the first trained generator function and one application of a second trained generator function, which acts as the inverse function to the first trained generator function) acts as identity mapping. What can be achieved by this is that the first trained generator function can create especially realistic differential image datasets.

According to a further embodiment of the invention the first trained generator function comprises an artificial neural network.

The inventors have recognized that even non-linear functions can be described efficiently by neural networks, in particular through the selection or the adaptation of edge weights as parameters, and the neural networks are especially suited to the processing of image data.

According to a further embodiment of the invention the first trained generator function comprises a residual value block, a shortcut connection, a convolutional layer, a deconvolutional layer, a pooling layer and/or a spatial transformer layer.

In a residual value block (an alternate name is residual value block) is a node layer of the neural network is not only connected with the directly following layer, nut also with one of the further subsequent layers. A connection with such a further subsequent layer is also referred to as a shortcut connection.

The use of residual blocks enables layers close to the input layer of the neural network to be better trained, and problems with disappearing gradients can be avoided.

A convolutional layer here in particular maps the mathematical operation of a convolution with one or more convolution kernels, wherein the elements of the convolution kernel correspond to weights of the neural network. A deconvolutional layer here in particular maps the mathematical operation of a deconvolution with one or more convolution kernels.

Convolutional layers are especially well suited to recognition and further processing of features of image datasets. In particular different features of the processed image datasets (e.g. edges or gradients) can be analyzed by different convolution kernels. Deconvolutional layers in particular enable predetermined features (e.g. edges or gradients) to be converted again into associated image datasets. In particular a suitable combination of convolutional layers and deconvolutional layers can act as an autoencoder.

A pooling layer can in particular be an upsampling layer or a downsampling layer. On application to an image dataset in an upsampling layer a pixel or a voxel is transformed into a number or pixels or voxels. On application to an image dataset a number or pixels or a number of voxels are transformed in a downsampling layer into one pixel or voxel.

Through the use of downsampling layers in particular the number of relevant features considered can be reduced, which in particular can prevent an overfitting. Through the use of upsampling layers a few features can in particular transformed again into an associated image dataset. In particular a suitable combination of downsampling layers and upsampling layers can act as an autoencoder.

Spatial transformer layers map geometrical transformations (e.g. rotation, translation, stretching, compression) of image datasets. Spatial transformer layers are known for example from Max Jaderberg et al., "Spatial Transformer Networks", arXiv:1506.02025v3 (2016), the entire contents of which are hereby incorporated herein by reference.

The use of one or more spatial transformation layers in particular enables first and second real image datasets or first real image datasets and mask image datasets that are not registered spatially to be registered in the network and thereby the accuracy or the robustness of networks to be increased for such image data.

In a second embodiment the invention relates to a computer-implemented method for provision of a first trained generator function. The method is based on a real image dataset and a comparison differential image dataset of the examination volume being received, in particular via a training interface. Furthermore a differential image dataset of the examination volume is determined by application of a first trained generator function to first input data, the first input data comprising the real image dataset here. Furthermore a first classification value is determined by application of a first trained classifier function to the differential image dataset, and a second classification value is determined by application of the first trained classifier function to the comparison differential image dataset, in particular via a training computing unit. Furthermore there is an adaptation of the first trained generator function and/or the first trained classifier function based on the first classification value and/or the second classification value, in particular likewise via the trainings computing unit. Furthermore there is a provision of the trained generator function, in particular via the training interface. The provision of the trained generator function can in particular comprise storage, transfer and/or display of the trained generator function.

The one classifier function in particular enables a distinction to be made between synthetic image datasets and real image datasets. A classification value in this case can in particular comprise a probability value, wherein the probability value corresponds to the probability of the input value of a classifier function corresponding to a real image dataset. The difference between 1 and the probability value then corresponds to the probability of the input value of the classifier function involving a synthetic image dataset.

The inventors have recognized that the method described enables a first trained generator function to be provided, which can convert a real image dataset into a differential image dataset, and which can be employed in a method for provision of a differential image dataset.

According to a further embodiment of the invention the method for provision of a first trained generator function comprises determining a first comparison real image dataset of the examination volume by application of a second trained generator function to second input data, in particular via the training computing unit. The second input data comprises the differential image dataset here. The method furthermore comprises an adaptation of the second trained generator function based on a cyclic consistency loss function, in particular via the training computing unit, wherein the cyclic consistency loss function is based on a comparison of the first real image dataset and the first comparison real image dataset.

The inventors have recognized that the use of a cyclic consistency loss function enables the second trained generator function to be adapted so that the first trained generator function and the second trained generator function interact in each case as inverse functions or act together as an autoencoder. This enables an especially high image quality of the image data created by the first trained generator function.

According to a further embodiment of the invention the method for provision of a first trained generator function comprises a receipt of a comparison mask image dataset of the examination volume, in particular via the training interface. The method further comprises a determination of a mask image dataset of the examination volume by applying the first trained generator function to the first input data, in particular via the training computing unit. The determination of the mask image dataset can take place here by the same application of the first trained generator function, through which the differential image dataset was also determined. In other words the application of the first trained generator function generates output data, which comprises the differential image dataset and the mask image dataset. The method furthermore comprises the determination of the first mask classification value by application of a trained mask classifier function to the mask image dataset and also the determination of a second mask classification value by application of a trained mask classifier function to the comparison mask image dataset, in each case in particular via the training computing unit. Furthermore the method comprises an adaptation of the first trained generator function and/or of the trained mask classifier function based on the first mask classification value and/or the second mask classification value.

The inventors have recognized that the method described also enables mask image datasets to be able to be included as well in the training of the first generator function. Since through this there are more relevant features or information present in the training, this enables the training to be improved.

According to a further embodiment of the invention the method for provision of a first trained generator function comprises a receipt of a training differential image dataset of the examination volume and a receipt of a training real image dataset of the examination volume, in particular via the training interface. Furthermore the method comprises a determination of a first synthetic real image dataset by application of a second trained generator function to second training input data, wherein the second training input data comprises the training differential image dataset. Furthermore the method comprises determination of a third classification value by application of a second trained classifier function to first synthetic real image dataset, as well as a determination of a fourth classification value by application of the second trained classifier function to the training real image dataset, in each case via the training computing unit. Furthermore the method comprises an adaptation of the second trained generator function and/or of the second trained classifier function based on the third classification value and/or the fourth classification value.

The inventors have recognized that through the adaptation of the second trained generator function and/or of the second trained classifier function based on the third classification value and/or the fourth classification value, it is possible to adapt in such a manner that the second trained generator function creates synthetic data, which can be classified by the second trained classifier function where possible as real data, and that the second trained classifier function can differentiate as well as possible between real and synthetic data. These opposing aims enable the two trained functions to be improved simultaneously.

According to a further embodiment of the invention the method for provision of a first trained generator function comprises a determination of a synthetic differential image dataset of the examination volume by application of the first trained generator function to first training input data, wherein the first training input data comprises the first synthetic real image dataset. Furthermore the method comprises an adaptation of the first trained generator function based on a cyclic consistency loss function, wherein the cyclic consistency loss function is based on a comparison of the training differential image dataset and the synthetic differential image dataset.

The inventors have recognized that the use of a cyclic consistency loss function enables the first trained generator function to be adapted so that the first trained generator function and the second trained generator function interact as inverse functions in each case or act together as an autoencoder. This enables an especially high image quality of the image data created by the first trained generator function to be achieved.

According to a further embodiment of the invention the method for provision of a first trained generator function comprises a receipt of a training mask image dataset of the examination volume, wherein the second training input data continues to comprise the training mask image dataset.

The inventors have recognized that the method described also enables mask image datasets to be included as well in the training of the first generator function. Since this enables more relevant features or information to be present in the training, the training can be improved by this.

According to a further embodiment of the invention, on application of the first trained generator function to the first training input data a synthetic mask image dataset is furthermore determined, wherein the cyclic consistency loss function is furthermore based on a comparison of training mask image dataset and the synthetic mask image dataset.

The inventors have recognized that the use of a cyclic consistency loss function enables the first trained generator function to be adapted so that the first trained generator function and the second trained generator function interact as inverse functions in each case, or act together as an autoencoder. This enables an especially high image quality of the image data created by the first trained generator function to be achieved.

According to a further embodiment of the invention the first trained generator function was provided in the method for provision of a differential image dataset by a method for provision of a first trained generator function in accordance with the invention or one of its embodiments.

In a third embodiment the invention relates to a provision system for provision of a differential image dataset of an examination volume, comprising an interface and a computing unit,
wherein the interface is embodied to receive a first real image dataset of the examination volume, wherein the examination volume comprises a vessel, wherein the first real image dataset comprising the examination volume maps contrast medium,
wherein the computing unit is embodied to determine the differential image dataset of the examination volume by application of a first trained generator function to input data,
wherein the input data comprises the first real image dataset,
wherein a parameter of the first trained generator function is based on a GA algorithm,
wherein the interface is furthermore embodied for provision of the differential image dataset.

Such a provision system can in particular be embodied for carrying out the inventive methods for provision of a differential image dataset and its embodiments described above. The provision system is embodied to carry out these methods and their embodiments, in that the interface and the computing unit are embodied to carry out the corresponding method steps.

In a possible fourth embodiment the invention relates to an x-ray facility, comprising an x-ray source and an x-ray detector, furthermore comprising a provision system according to the third embodiment of the invention. An x-ray facility can in particular involve a C-arm x-ray facility or a computed tomography unit.

In a possible fifth embodiment the invention relates to a training system for provision of a first trained generator function, comprising a training interface and a training computing unit,
wherein the training interface is embodied to receive a first real image dataset of an examination volume,
wherein the training interface is furthermore embodied to receive a comparison differential image dataset of the examination volume,
wherein the computing unit is embodied to determine a differential image dataset of the examination volume by application of a first trained generator function to first input data,
wherein the first input data comprises the first real image dataset,
wherein the computing unit is furthermore embodied to determine a first classification value by application of a first trained classifier function to the differential image dataset,
wherein the computing unit is furthermore embodied to determine a second classification value by application of the first trained classifier function to the comparison differential image dataset,
wherein the computing unit is furthermore embodied to adapt the first trained generator function and/or the first trained classifier function based on the first classification value and/or the second classification value,
wherein the training interface is furthermore embodied for provision (PRV-GF-1) of the first trained generator function (GF-1).

Such a training system can in particular be embodied to carry out the inventive methods for provision of a first trained generator function and their embodiments described above. The training system is embodied to carry out these methods and their embodiments, in that the interface and the computing unit are embodied to carry out the corresponding method steps.

In a sixth embodiment the invention relates to a computer program product with a computer program, which is able to be loaded directly into a memory of a provision system, with program sections for carrying out all steps of the method for provision of a differential image dataset and its embodiments when the program sections are executed by the provision system; and/or which is able to be loaded directly into a memory of a training system, with program sections for carrying out all steps of the method for provision of a differential image dataset and its embodiments when the program sections are executed by the training system.

In particular the invention relates to a computer program product with a computer program, which is able to be loaded directly into a memory of a provision system, with program sections for carrying out all steps of the method for provision of a differential image dataset and its embodiments when the program sections are executed by the provision system.

In particular the invention relates to a computer program product with a computer program, which is able to be loaded directly into a training memory of a training system, with program sections for carrying out all steps of the method for provision of a first trained generator function and its embodiments when the program sections are executed by the training system.

In a seventh embodiment the invention relates to a computer-readable storage medium, on which program sections able to be read and executed by a provision system are stored, in order to carry out all steps of the method for provision of a differential image dataset and its embodiments when the program sections are executed by the provision system; and/or on which program sections able to be read and executed by a training system are stored, in order to carry out all steps of the method for provision of a first trained generator function and its embodiments when the program sections are executed by the training system.

In particular the invention relates to a computer-readable storage medium, on which program sections able to be read and executed by a provision system are stored, in order to carry out all steps of the method for provision of a first trained generator function and its embodiments when the program sections are executed by the provision system.

In particular the invention relates to a computer-readable storage medium, on which program sections able to be read and executed by a training system are stored, in order to carry out all steps of the method for provision of a first trained generator function and its embodiments when the program sections are executed by the training system.

In an eighth embodiment the invention relates to a computer program or a computer-readable storage medium, comprising a first trained generator function, provided by a method for provision of a first trained generator function.

A largely software-based realization has the advantage that even provision systems and training systems already used previously can be upgraded retrospectively in a simple manner by a software update in order to work in the inventive way. Such a computer program product, as well as the computer program, can possibly comprise additional elements such as e.g. documentation and/or additional components, as well as hardware components, such as e.g. hardware keys (dongles etc.) for use of the software.

FIG. 1 shows a first data flow diagram for use in a method for provision of a differential image dataset DDS and/or in a method for provision of a first trained generator function GF-1.

The first trained generator function GF-1 is applied in the first data flow diagram in a first variant to a first real image dataset RDS-1, the first trained generator function GF-1 is applied in the first data flow diagram in a second variant to the first real image dataset RDS-1 and to a second real image dataset RDS-2. In both variants the output data of the first trained generator function GF-1 comprises a differential image dataset DDS.

If $X_{fill,1}$ refers to the first real image dataset RDS-1, $X_{fill,2}$ to the second real image dataset RDS-2, and $Y_{DSA}$ to the differential image dataset DDS, then it is true that in the first variant $Y_{DSA}=GF\text{-}1(X_{fill,1})$, and in the second variant $Y_{DSA}=GF\text{-}1(X_{fill,1}, X_{fill,2})$. B refers below to the space of the image datasets. For example for two-dimensional image datasets the space of the image datasets can be $B=R^{m \cdot n}$ (wherein R refers to the real numbers and m or n to the number of the pixels or voxels for each of the dimensions), for three-dimensional image datasets the space of the image datasets can be $B=R^{i \cdot j \cdot k}$ (wherein i, j and k refer to the number of the pixels or voxels for each of the dimensions). In the first variant first trained generator function GF-1 is thus a function GF-1: $B \rightarrow B$, and in the second variant the first trained generator function GF-1 is a function GF-1: $B^2 \rightarrow B$.

As an alternative it is possible for the input data of the first trained generator function GF-1 to comprise further real image datasets of the examination volume. In this further variant the first trained generator function GF-1 is thus a function GF-1: $B^n \rightarrow B$, wherein n refers to the number of the real image datasets of the input data of the first trained generator function GF-1.

The data flow described above in the first data flow diagram describes in particular the data flow in the method for provision of the differential image dataset DDS. The further elements of the first data flow diagram in particular describe the data flow in the method for provision of the first trained generator function GF-1.

In the first data flow diagram a first trained classifier function DF-1 is furthermore applied to the differential image dataset DDS, the result of the application is a probability value. Furthermore the first classifier function DF-1 is applied to a comparison differential dataset DDS-C of the examination volume, the result of the application is a comparison probability value.

If $Y^{(C)}_{DSA}$ refers to the comparison differential dataset DDS-C, then for the probability value $p=DF\text{-}1(Y_{DSA})=DF\text{-}1(Y_{DSA})=GF\text{-}1(X_{fill,1})$ or $p=DF\text{-}1(Y_{DSA})=DF\text{-}1(Y_{DSA})=GF\text{-}1(X_{fill,1}, X_{fill,2})$, and for the comparison probability value $p^{(C)}=DF\text{-}1(Y^{(C)}_{DSA})$. The first classifier function DF-1 is thus in particular a function DF-1: $B \rightarrow [0, 1]$.

The probability value and the comparison probability value can be used here in an adversarial loss function, either together or separately. Based on this adversarial loss function AL the first trained generator function GF-1 and the first trained classifier function DF-1 can be adapted, in particular this adversarial loss function AL can be optimized by adaptation of the respective parameters.

In the first data flow diagram a second trained generator function GF-2 is furthermore applied to the differential image dataset DDS, the result of the application is in the first variant a first comparison real image dataset RDS-1-C, the result of the application in the second variant is the first comparison image dataset RDS-1-C and a second comparison real image dataset RDS-2-C.

If $X^{(C)}_{fill,1}$ refers to the first comparison real image dataset RDS-C-1, and if $X^{(C)}_{fill,2}$ refers to the second comparison real image dataset RDS-C-2, then in the first variant $X^{(C)}_{fill,1}=GF\text{-}2(Y_{DSA})$ in the second variant $(X^{(C)}_{fill,1}, X^{(C)}_{fill,2})=GF\text{-}2(Y_{DSA})$. The second trained generator function GF-2 is thus in the first variant a function GF-2: $B \rightarrow B$, and in the second variant a function GF-2: $B \rightarrow B^2$. If yet further real image datasets are used, the second trained generator function GF-2 is a function GF-2: $B \rightarrow B^n$. In particular the second trained generator function GF-2 can be expressed as an inverse function of the first trained generator function GF-1.

The first comparison real image dataset RDS-1-C can be used here together with the first real image dataset RDS-1 in the computation of a cyclic consistency loss function CCL. Based on this cyclic consistency loss function CCL the second trained generator function GF-2 can be adapted, in particular this cyclic consistency loss function CCL can be optimized by adaptation of the respective parameters.

Figure 2:
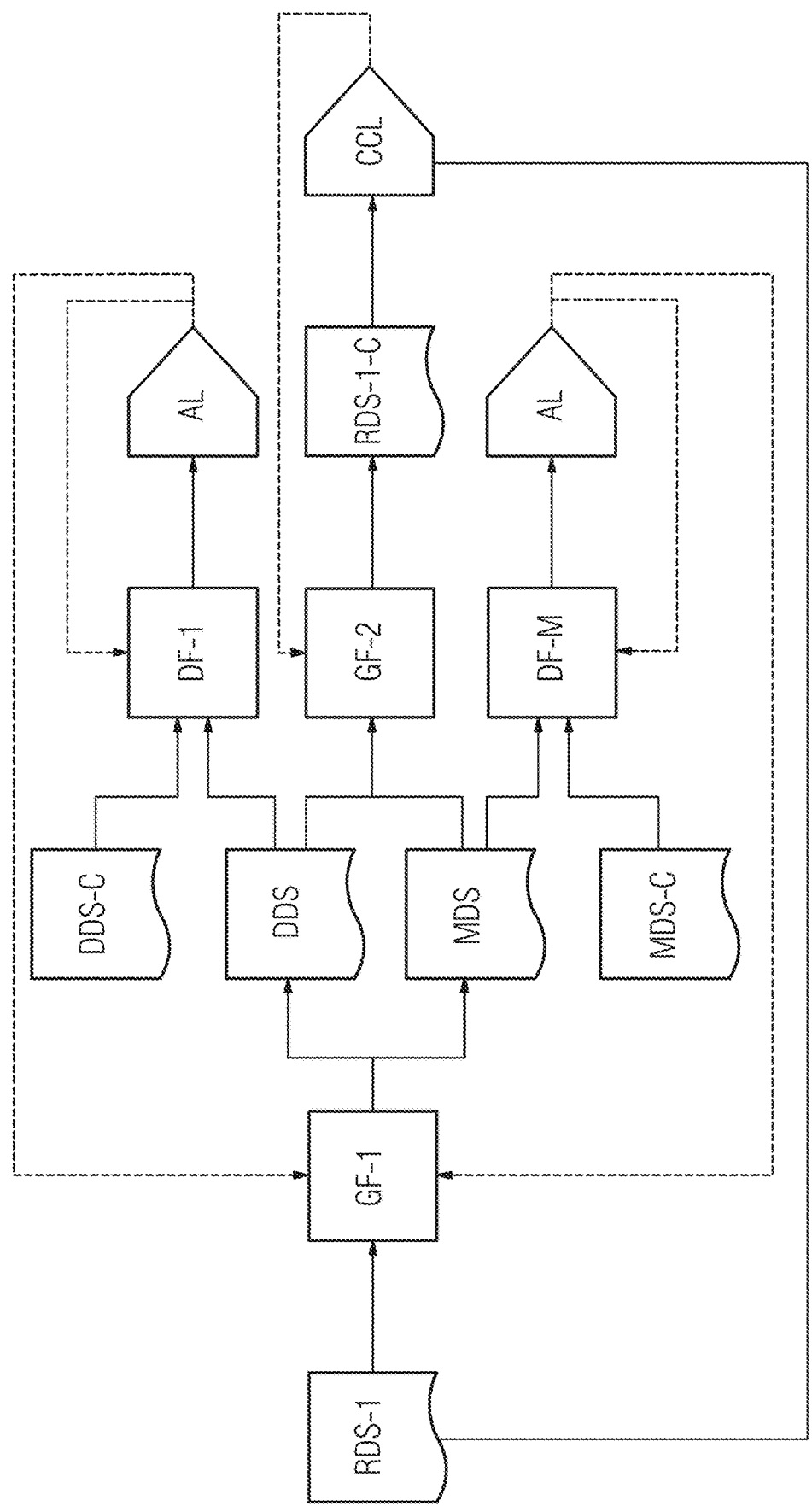
FIG. 2 shows a second data flow diagram of the method in accordance with the invention and its embodiments.

FIG. 2 shows a second data flow diagram for use in a method for provision of a differential image dataset DDS and/or in a method for provision of a first trained generator function GF-1. The second data flow diagram has elements that have already been described in relation to FIG. 1 or in relation to the first data flow diagram. Unless stated otherwise the elements of the second data flow diagram can have all embodiments and further developments of the corresponding elements of the first data flow diagram.

Unlike in the first data flow diagram the first trained generator function GF-1 in the second data flow diagram creates a mask image dataset MDS as an output value as well as the differential image dataset DDS. If M refers to the mask image dataset, then thus $(Y_{DSA}, M)=GF-1(X_{fill,1})$. As an alternative the first trained generator function GF-1 can also be applied to a number of real image datasets RDS-1, RDS-2. The first trained generator function GF-1 is thus a function GF-1: $B \to B^2$.

As well as the first trained classifier function DF-1 there exists in the second data flow diagram a trained mask classifier function DF-M, which is applied to the mask image dataset MDS or to a comparison mask image dataset MDS-C. In the application to the mask image dataset MDS a probability value is established here, in the application to the comparison mask image dataset MDS-C a comparison probability value is established here.

If $M^{(C)}$ refers to the comparison mask image dataset MDS-C, then for the probability value r=DF-M(M) applies, and for the comparison probability value $r^{(C)}$=DF-M($M^{(C)}$) applies. The trained mask classifier function DF-M is thus in particular a function DF-1: $B \to [0, 1]$.

The probability value and the comparison probability value can be used here in an adversarial loss function, either together or separately. Based on this adversarial loss function AL the first trained generator function GF-1 and the trained mask classifier function DF-M can be adapted, in particular this adversarial loss function AL can be optimized by adapting the respective parameters.

In the second data flow diagram the second trained generator function GF-2 is furthermore applied to the differential image dataset DDS and the mask image dataset MDS, the result of the application is a first comparison real image dataset RDS-1-C. Thus $X^{(C)}_{fill,1}=GF-2(Y_{DSA}, M)$, and the second trained generator function GF-2 is a function GF-2: $B \to B^2$. In particular the second trained generator function GF-2 can be expressed as the inverse function of the first trained generator function GF-1.

The first comparison real image dataset RDS-1-C can be used here together with the first real image dataset RDS-1 for computation of a cyclic consistency loss function CCL. Based on this cyclic consistency loss function CCL the second trained generator function GF-2 can be adapted, in particular this cyclic consistency loss function CCL can be optimized by the adaptation of the respective parameters.

Figure 3:
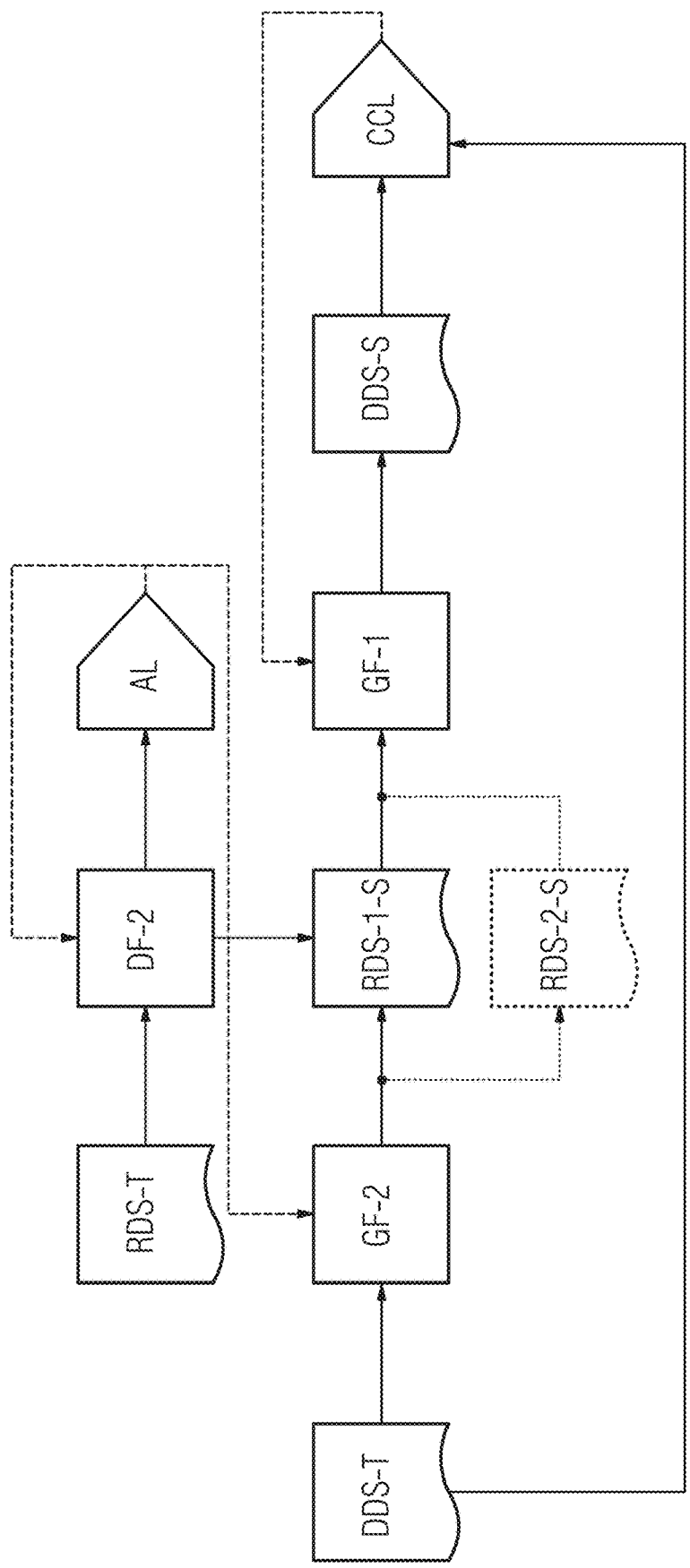
FIG. 3 shows a third data flow diagram of the method in accordance with the invention and its embodiments.

FIG. 3 shows a third data flow diagram for use in a method for provision of a differential image dataset DDS and/or in a method for provision of a first trained generator function GF-1. The first data flow diagram and the third data flow diagram can be used in particular together in a method for provision of a differential image dataset DDS and/or in a method for provision of a first trained generator function GF-1.

The second trained generator function GF-2 is applied in the third data flow diagram to a training differential image dataset DDS-T, in a first variant the output data comprises a first synthetic real image dataset RDS-1-S, in a second variant the output data comprises the first synthetic real image dataset RDS-1-S and a second synthetic real image dataset RDS-2-S. The training differential image dataset DDS-T can have all embodiments and developments of a differential image dataset DDS, the first or the second synthetic real image dataset RDS-1-S, RDS-2-S can have all embodiments and developments of a first or a second real image dataset RDS-1, RDS-2.

If $Y^{(T)}_{DSA}$ refers to the training differential image dataset DDS-T, $X^{(S)}_{fill,1}$ refers to the first synthetic real image dataset RDS-1-S, and $X^{(S)}_{fill,2}$ refers to the second synthetic real image dataset RDS-2-S, then in the first variant $X^{(S)}_{fill,1}=GF-2(Y^{(T)}_{DSA})$ applies, in the second variant $(X^{(S)}_{fill,1}, X^{(S)}_{fill,2})=GF-2(Y^{(T)}_{DSA})$ applies. The second trained generator function GF-2 is thus in the first variant a function GF-2: $B \to B$, and in the second variant a function GF-2: $B \to B^2$. If yet further real image datasets are used, the second trained generator function GF-2 is a function GF-2: $B \to B^n$.

The first trained generator function GF-1 is applied in the third data flow diagram in a first variant to the first synthetic real image dataset RDS-1-S, the first trained generator function GF-1 is applied in the third data flow diagram in a second variant to the first synthetic real image dataset RDS-1-S and to the second synthetic real image dataset RDS-2-S. In both variants the output data of the first trained generator function GF-1 comprises a synthetic differential image dataset DDS-S.

If $Y^{(S)}_{DSA}$ refers to the synthetic differential image dataset DDS-S, then thus in the first variant $Y^{(S)}_{DSA}=GF-1(X^{(S)}_{fill,1})$ applies, and in the second variant gilt $Y^{(S)}_{DSA}=GF-1(X^{(S)}_{fill,1}, X^{(S)}_{fill,2})$ applies. In the first variant the first trained generator function GF-1 is thus a function GF-1: $B \to B$, and in the second variant the first trained generator function GF-1 is a function GF-1: $B^2 \to B$. If yet further real image datasets are used, the first trained generator function GF-1 is a function GF-1: $B^n \to B$.

The synthetic differential image dataset DDS-S can be used here together with the training differential image dataset DDS-T in a cyclic consistency loss function. Based on this cyclic consistency loss function CCL the first trained generator function GF-1 can be adapted, in particular this cyclic consistency loss function CCL can be optimized by adaptation of the respective parameters.

In the third data flow diagram a second trained classifier function DF-2 is furthermore applied to the first synthetic real image dataset RDS-1-S, the result of the application is a probability value. The second trained classifier function DF-2 is furthermore applied to a training real image dataset RDS-T of the examination volume VOL, the result of the application is a comparison probability value.

If $X^{(T)}_{fill}$ refers to the first training real image dataset RDS-T, then for the probability value $q=DF-2(X^{(S)}_{fill,1})$ applies, and for the comparison probability value $q^{(C)}=DF-2(X^{(T)}_{fill})$ applies. The second trained classifier function DF-2 is thus in particular a function DF-1: $B \to [0, 1]$.

The probability value and the comparison probability value can be used here in an adversarial loss function, either together or separately. Based on this adversarial loss function AL the second trained generator function GF-2 and the second trained classifier function DF-2 can be adapted, in particular this adversarial loss function AL can be optimized by adaptation of the respective parameters.

Figure 4:
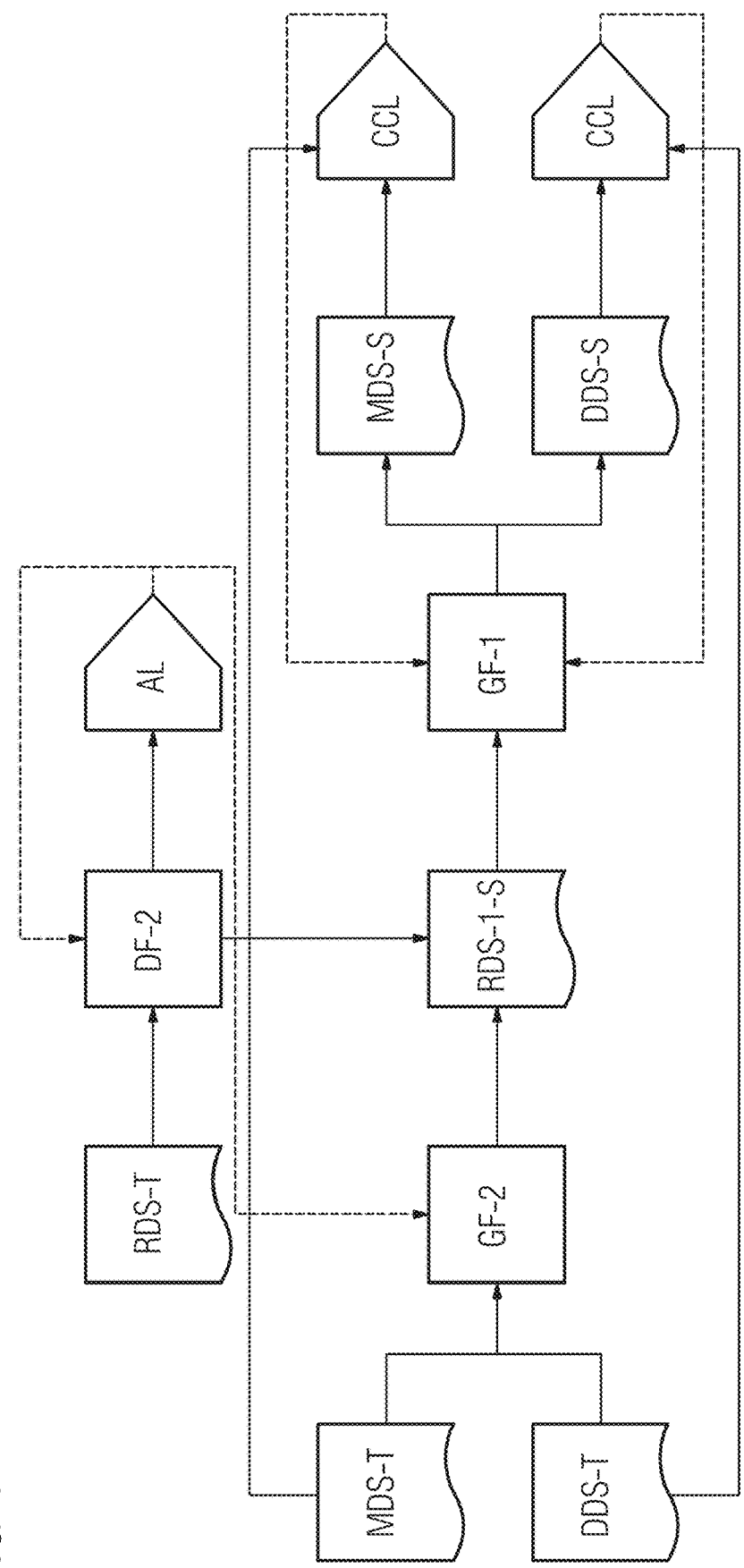
FIG. 4 shows a fourth data flow diagram of the method in accordance with the invention and its embodiments.

FIG. 4 shows a fourth data flow diagram for use in a method for provision of a differential image dataset DDS and/or in a method for provision of a first trained generator function GF-1. The fourth data flow diagram has elements that have already been described in relation to FIG. 3 or in relation to the third data flow diagram. Unless stated otherwise, the elements of the second data flow diagram can have all embodiments and developments of the corresponding elements of the first data flow diagram. The second data flow diagram and the fourth data flow diagram can in particular be used together in a method for provision of a differential image dataset DDS and/or in a method for provision of a first trained generator function GF-1.

The second trained generator function GF-2 is applied in the fourth data flow diagram to a training differential image dataset DDS-T and to a training mask image dataset MDS-T, the output data comprises a first synthetic real image dataset RDS-1-S. Thus $X^{(S)}_{fill,1}=GF\text{-}2(Y^{(T)}_{DSA}, M^{(T)})$ applies. The second trained generator function GF-2 is thus a function GF-2: $B^2 \rightarrow B$.

The first trained generator function GF-1 is applied in the fourth data flow diagram to the first synthetic real image dataset RDS-1-S. The output data of the first trained generator function GF-1 comprises a synthetic differential image dataset DDS-S and a synthetic mask image dataset MDS-S. If $M^{(S)}$ refers to the synthetic mask image dataset MDS-S, then thus $(Y^{(S)}_{DSA}, M^{(S)})=GF\text{-}1(X^{(S)}_{fill,1})$ applies. The first trained generator function GF-1 is thus a function GF-1: $B \rightarrow B^2$.

The synthetic mask image dataset MDS-S can be used here together with the training mask image dataset MDS-T in a cyclic consistency loss function CCL, likewise the comparison differential dataset DDS-C together with the training differential image dataset DDS-T can be used in the cyclic consistency loss function CCL. Based on this cyclic consistency loss function CCL the first trained generator function GF-1 can be adapted, in particular this cyclic consistency loss function CCL can be optimized by adaptation of the respective parameters.

Figure 5:
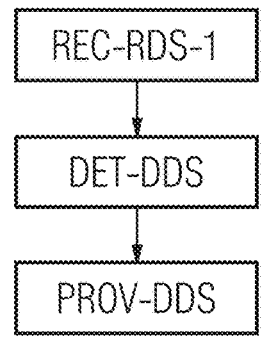
FIG. 5 shows a first example embodiment of a method for provision of a differential image dataset of an examination volume.

FIG. 5 shows a first example embodiment of a method for provision of a differential image dataset DDS of an examination volume VOL. The first example embodiment shown can implement the first data flow diagram shown in FIG. 1.

The first step of the first example embodiment shown is the receipt REC-RDS-1 of a first real image dataset RDS-1 of the examination volume VOL. Here the examination volume VOL comprises a vessel, and the first real image dataset RDS-1 maps the examination volume VOL comprising the contrast medium. The receipt REC-RDS-1 of the first real image dataset RDS-1 is undertaken in particular via a interface IF of a provision system PRVS.

In this example embodiment the first real image dataset RDS-1 is an image dataset in accordance with the DICOM (acronym for "Digital Imaging and Communications in Medicine") standard. In particular the first real image dataset RDS-1 is a two-dimensional image dataset, and can have an extent of 512×512 pixels for example. As an alternative the first real image dataset RDS-1 can also be a three-dimensional image dataset, and can have an extent of 512×512× 512 voxels for example. In particular here each pixel and/or each voxel can be assigned an intensity value, in particular an x-ray intensity value, which are based on the x-ray absorption coefficients of the examination volume VOL. As an alternative the first real image dataset RDS-1 can have another dimensionality, another extent and/or another format.

The second step of the first example embodiment shown is the determination DET-DDS of the differential image dataset DDS of the examination volume VOL by application of a first trained generator function GF-1 to input data. Here the input data comprises the first real image dataset RDS-1, and a parameter of the first trained generator function GF-1 based on a GA algorithm. The determination DET-DDS of the differential image dataset DDS is undertaken in particular via a computing unit CU of the provision system PRVS.

In this first example embodiment the differential image dataset DDS in particular has the same dimensionality and the same extent as the first real image dataset RDS-1, can thus in particular be a two-dimensional image dataset with an extent of 512×512 pixels, or a three-dimensional image dataset with an extent of 512×512×512 pixels. In particular the differential image dataset DDS corresponds, at least approximately, to the difference between the first real image dataset RDS-1 and an image dataset that maps the examination volume VOL in relation to the same mapping geometry as the first real image dataset RDS-1, wherein the examination volume VOL does not include any contrast medium however. In particular the differential image dataset DDS is also an image dataset in accordance with the DICOM standard.

In this example embodiment the first trained generator function GF-1 has in particular been trained together with a trained classifier function DF-1, DF-2 in or via a GA algorithm. In particular the first trained generator function GF-1 has been trained here in such a way that the synthetic data of the trained classifier function DF-1, DF-2 created by the first trained generator function GF-1 can if possible not be distinguished from real data.

In this example embodiment the first real image dataset RDS-1 has a first noise level, and the differential image dataset DDS has a second noise level. The first noise level here is higher than the second noise level. In this example embodiment the noise level is the inverse value of the signal-to-noise ratio. The characteristic of the first trained generator function GF-1 of reducing noise of the noise level can in particular be achieved, in the training of the trained generator function GF-1, by this being applied to image datasets with high noise level, and the result of this application (via a trained classifier function DF-1, DF-2) compared with differential images with a low noise level.

In this example embodiment there is advantageously patch-wise application of the first trained generator function GF-1 to the first real image dataset RDS-1. If for example $X_{fill}^{(1)}, \ldots, X_{fill}^{(K)}$ refers to patches of the first real image dataset RDS-1, then patches of the differential image dataset DDS can be computed as $Y_{DSA}^{(k)}=GF\text{-}1(X_{fill}^{(k)})$, with $1 \leq k \leq K$. The differential image dataset DDS can then be put together from the patches $Y_{DSA}^{(1)}, \ldots, Y_{DSA}^{(K)}$. If the first real image dataset RDS-1 is a two-dimensional image dataset with 512×512 pixels for example, this can be divided into four disjunct patches with 256×256 pixels for example.

In this example embodiment the first trained generator function GF-1 comprises an artificial neural network or the first trained generator function GF-1 comprises an artificial neural network. Advantageously this artificial neural network comprises a residual block, a shortcut connection, a convolutional layer, a deconvolutional layer, a pooling layer and/or spatial transformer layer. Furthermore in this example embodiment a cyclic consistency loss function has been minimized for training the first trained generator function GF-1, through this in particular a parameter or the first trained generator function GF-1 is based on this cyclic consistency loss function. Furthermore in training the first trained generator function GF-1 an adversarial loss function AL can have been minimized.

The third step of the first example embodiment shown is the provision PRV-DDS of the differential image dataset DDS, in particular via the interface IF of the provision system PRVS. In this first example embodiment the differential image dataset DDS is shown, in particular to make a diagnosis of the vessel possible. As an alternative the differential image dataset DDS can also be stored, or transferred to another system.

Figure 6:
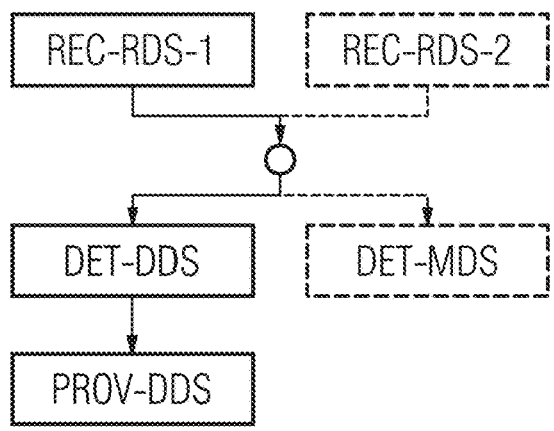
FIG. 6 shows a second example embodiment of a method for provision of a differential image dataset of an examination volume.

FIG. 6 shows a second example embodiment of a method for provision of a differential image dataset DDS of an examination volume VOL. The second example embodiment in particular implements the first or second data flow diagram shown in FIG. 1 or FIG. 2. The second example embodiment in particular comprises all steps of the first example embodiment of the method for provision of a differential image dataset DDS shown in FIG. 5, and can include all embodiments and developments described there.

The second example embodiment furthermore comprises a receipt REC-RDS-2 of a second real image dataset RDS-2 of the examination volume VOL, in particular via the interface IF of the provision system PRVS, and/or the determination of a mask image dataset MDS of the examination volume VOL, in particular via the computing unit CU of the provision system PRVS.

If the second example embodiment comprises the receipt REC-RDS-2 of a second real image dataset RDS-2 of the examination volume, then the first real image dataset RDS-1 maps the examination volume VOL at a first point in time, and the second real image dataset RDS-2 maps the examination volume VOL at a second point in time. The first point in time and the second point in time here are in particular different. Furthermore the input data in this case comprises the second real image dataset RDS-2. In particular the examination volume VOL includes contrast medium during the first point in time and during the second point in times. The spatial distribution of the contrast medium in the examination volume VOL at the first point in time can differ from the spatial distribution of the contrast medium in the examination volume VOL at the second point in time, however as an alternative, the spatial distributions can also be identical.

In this example embodiment the first real image dataset RDS-1 and the second real image dataset RDS-2 have an identical dimensionality and an identical extent. Furthermore in this example embodiment the first real image dataset RDS-1 and the second real image dataset RDS-2 have the same mapping geometry of the examination volume VOL, in particular an identical projection direction in relation to the examination volume VOL. For example the first real image dataset RDS-1 and the second real image dataset RDS-2 can thus have been recorded via an x-ray source XSYS.SRC and an x-ray detector XSYS.DTC, which have not changed their positions and alignments in relation to the examination volume VOL. As an alternative the first real image dataset RDS-1 and the second real image dataset can have a different mapping geometry RDS-2 in relation to the examination volume VOL. For example the first real image dataset RDS-1 and the second real image dataset RDS-2 can have been recorded during a rotation of the x-ray source XSYS-.SRC and/or of the x-ray detector XSYS.DTC about the examination volume VOL, for example via a C-arm x-ray facility XSYS or via a computed tomography unit.

If the second example embodiment comprises a determination DET-MDS of a mask image dataset MDS of the examination volume by application of the first trained generator function GF-1 to the input data, then the mask image dataset MDS maps the examination volume VOL in particular without contrast medium. In other words the mask image dataset MDS is an image dataset of the examination volume VOL without contrast medium. The mask image dataset MDS is in particular a synthetic image dataset.

In this example embodiment the first real image dataset RDS-1 and the mask image dataset MDS have an identical dimensionality and an identical extent. Furthermore in this example embodiment the first real image dataset RDS-1 and the mask image dataset VOL have the same mapping geometry in relation to the examination volume, in particular an identical projection direction in relation to the examination volume VOL.

Figure 7:
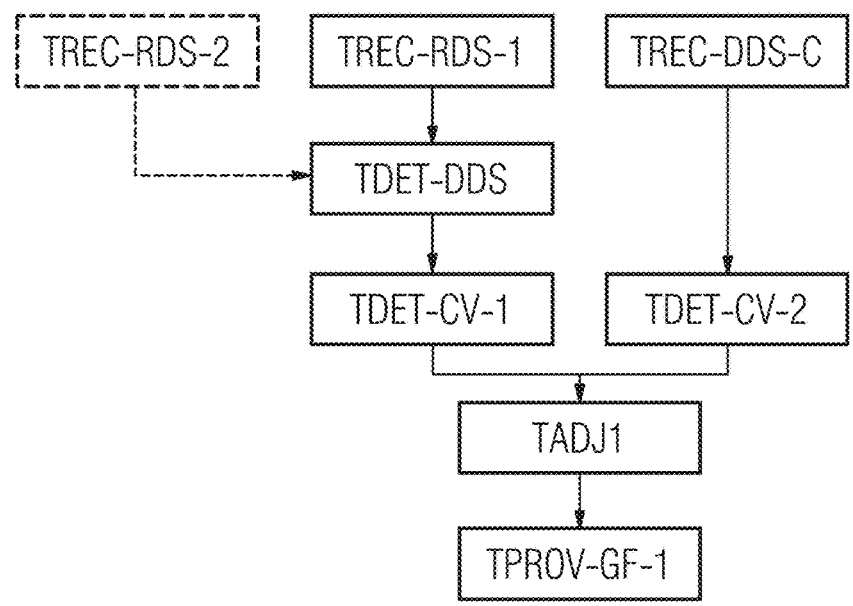
FIG. 7 shows a first example embodiment of a method for provision of a first trained generator function.

FIG. 7 shows a first example embodiment of a method for provision of a first trained generator function GF-1. The first example embodiment can in particular implement one or more of the data flow diagrams shown in FIG. 1 to FIG. 4.

The first steps of the first example embodiment are the receipt TREC-RDS-1 of a first real image dataset RDS-1 of an examination volume VOL, as well as the receipt TREC-DDS-C of a comparison differential image dataset DDS-C of the examination volume VOL, via a training interface TIF of the training system TSYS in each case. Optionally the first example embodiment can receive a receipt TREC-RDS-2 of a second real image dataset RDS-2 of the examination volume, in particular via the training interface TIF of the training system TSYS.

Thus pairs of training data can be received in particular via the training interface TIF, comprising the first real image dataset RDS-1 and the comparison differential dataset DDS-C. In this example embodiment a pair of training data is received in each case, as an alternative a number of pairs of training data can also be received. If a second real image dataset RDS-2 is received, then a pair of training data comprises the real image datasets RDS-1, RDS-2 as well as a comparison differential dataset DDS-C.

The first real image dataset RDS-1 and the comparison differential dataset DDS-C have the same dimensionality. In this example embodiment the first real image dataset RDS-1 and the comparison differential dataset DDS-C are two-dimensional image datasets. As an alternative three-dimensional or four-dimensional image datasets can also be involved here. Furthermore the real image dataset RDS-1 and the comparison differential dataset DDS-C, in particular in relation to each of the dimensions, have an identical extent measured in pixels or voxels. For example in this example embodiment both the first real image dataset RDS-1 and the comparison differential dataset DDS-C can have an extent of 512×512 pixels.

The optional second real image dataset RDS-2 in particular likewise has the same dimensionality, and in relation to each of the dimensions the same extent measured in pixels or voxels as the first real image dataset RDS-1. For example the second real image dataset RDS-2 can have an extent of 512×512 pixels.

In particular the comparison differential dataset DDS-C corresponds at least approximately to the difference between the first real image dataset RDS-1 and an image dataset, which maps the examination volume VOL as regards the same mapping geometry as the first real image dataset RDS-1, wherein the examination volume VOL does not include any contrast medium however. Furthermore the comparison differential dataset DDS-C has a lower noise value than the first real image dataset RDS-1.

In particular in this example embodiment the first real image dataset RDS-1 and the comparison differential dataset DDS-C are image datasets in accordance with the DICOM standard. The optional second real image dataset can also be an image dataset in accordance with the DICOM standard.

A further step of the first example embodiment is the determination TDET-DDS of a differential image dataset DDS of the examination volume VOL by application of a first trained generator function GF-1 to first input data, wherein the first input data comprises the first real image dataset RDS-1. The determination TDET-DDS of the differential image dataset DDS is undertaken in particular via a training computing unit TCU of the training system TSYS. If $X_{fill,1}$ refers to the first real image dataset RDS-1 and $Y_{DSA}$ to the differential image dataset DDS, then thus $Y_{DSA}$=GF-$1(X_{fill,1})$ applies here.

In this first example embodiment the differential image dataset DDS in particular has the same dimensionality and the same extent as the first real image dataset RDS-1, thus in particular can be a two-dimensional image dataset with an extent of 512×512 pixels.

In the variant of the example embodiment in which a second real image dataset RDS-2 is present, the input data can furthermore in particular comprise the second real image dataset RDS-2. If $X_{fill,2}$ refers to the second real image dataset RDS-2 and $Y_{DSA}$ to the differential image dataset DDS, then thus $Y_{DSA}$=GF-1($X_{fill,1}$, $X_{fill,2}$) applies here.

Further steps of the first example embodiment are the determination TDET-CV-1 of a first classification value by application of a first trained classifier function DF-1 to the differential image dataset DDS, and also the determination TDET-CV-2 of a second classification value by application of the first trained classifier function DF-1 to the comparison differential dataset DDS-C, via the training computing unit TCU of the training system TSYS in each case.

The first classification value here is a probability value p, this corresponds to the probability estimated by the first classifier function DF-1 that the differential image dataset DDS is a real image dataset. The second classification value here is a probability value $p^{(c)}$, this corresponds to the probability estimated by the first classifier function DF-1 that the comparison differential dataset DDS-C is a real image dataset. Thus, in this example embodiment p=DF-1 ($Y_{DSA}$)=DF-1(GF-1($X_{fill,1}$, $X_{fill,2}$)) or p=DF-1($Y_{DSA}$)=DF-1 (GF-1($X_{fill,1}$)) and $p^{(c)}$=DF-1($Y^{(c)}_{DSA}$) apply, wherein $Y^{(c)}_{DSA}$ refers to the comparison differential dataset DDS-C.

In this example embodiment the first trained classifier function DF-1 is an artificial neural network or the first trained classifier function DF-1 comprises an artificial neural network. Advantageously this artificial neural network comprises a residual block, a shortcut connection, a convolutional layer, a deconvolutional layer, a pooling layer and/or a spatial transformer layer. Furthermore, in the training of the first trained classifier function DF-1 an adversarial loss function AL can have been minimized.

A further step of the example embodiment shown is the adaptation TADJ-1 the first trained generator function GF-1 and/or of the first trained classifier function DF-1 based on the first classification value and/or the second classification value, in particular via the training computing unit TCU of the training system TSYS.

In this first example embodiment the first trained generator function GF-1 is adapted, in that one or more parameters of the first trained generator function GF-1 are adapted for optimizing, in particular for minimizing, a loss function $K^{(GF-1)}$. Furthermore the first trained classifier function DF-1 is adapted, in that one or more parameters of the first trained classifier function DF-1 are adapted for optimizing, in particular for minimizing, a loss function $K^{(DF-1)}$. A gradient descent and a backpropagation are used in particular for the minimization.

The loss function $K^{(DF-1)}$ here is identical to an adversarial loss function $K^{(DF-1)}_A$=−BCE(DF-1($Y^{(c)}$), 1)−BCE (DF-1(Y), 0)=−BCE($p^{(c)}$, 1)−BCE(p, 0), wherein BCE refers to the binary cross-entropy with BCE(z, z')=z' log(z)+ (1−z')log(1−z). In particular the adversarial loss function $K^{(DF-1)}_A$ is thus given by $K^{(DF-1)}_A$=−log(DF-1($Y^{(c)}$))−log(1− DF-1(Y))=−log($p^{(c)}$)−log(1−p). In a minimization of this loss function the first trained classifier function DF-1 is embodied to distinguish as well as possible between real image data (corresponding to the comparison differential image datasets DDS-C) and synthetic image data (corresponding to the differential image datasets DDS) created by the first trained generator function GF-1.

In particular an adversarial loss function $K^{(GF-1)}_A$=−BCE (DF-1(Y), 1)=−log(p) can likewise be used for the loss function $K^{(GF-1)}$ of the first trained generator function GF-1. In a minimization of this loss function the first trained generator function GF-1 is embodied to create such differential image datasets DDS as are incorrectly classified by the first trained classifier function DF-1 as real image data.

The last step of the first example embodiment is the provision PRV-GF-1 of the first trained generator function GF-1 via the training interface TIF of the training system TSYS. In particular here the first trained generator function GF-1 can be transferred to a provision system PRVS.

Figure 8:
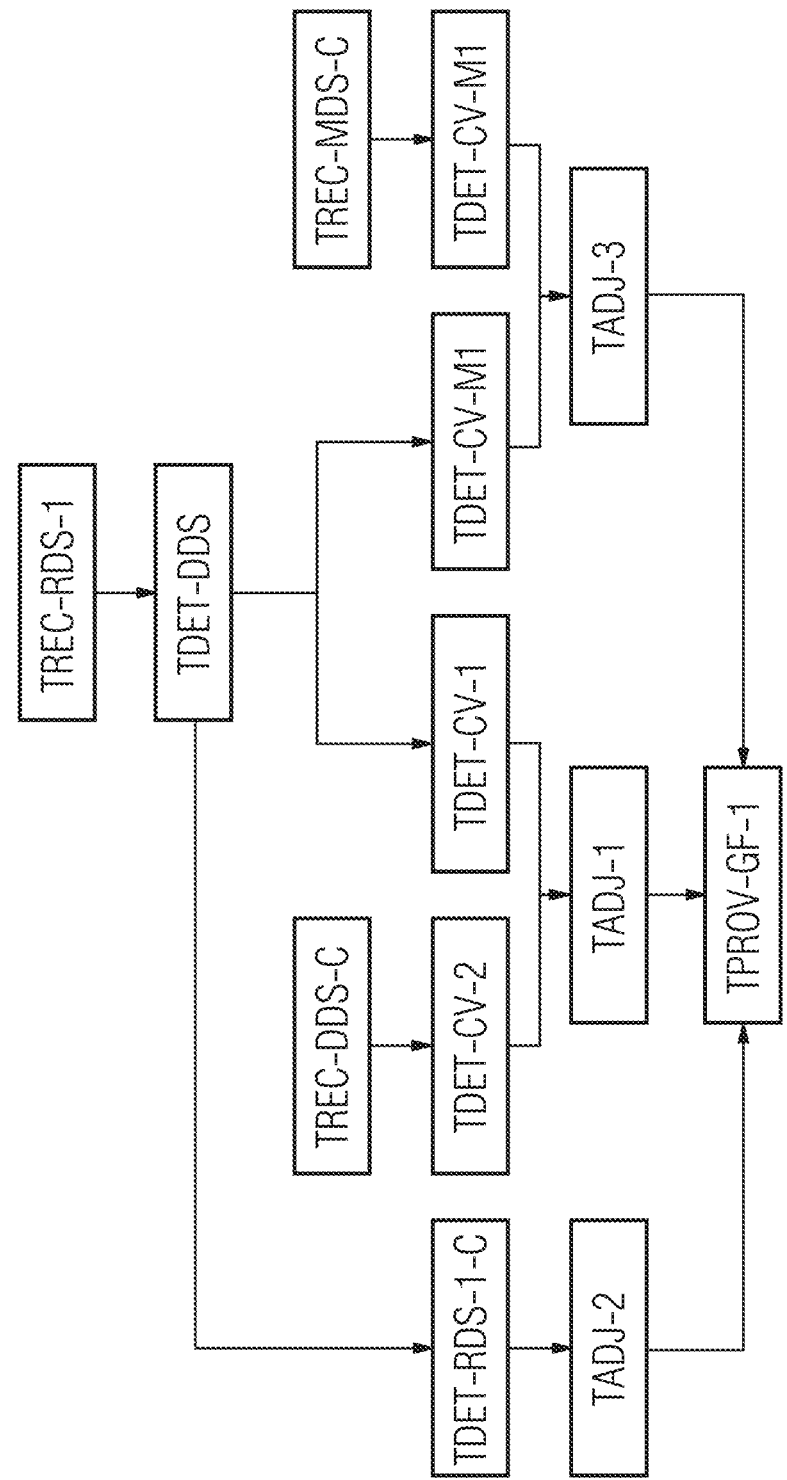
FIG. 8 shows a second example embodiment of a method for provision of a first trained generator function.

FIG. 8 shows a second example embodiment of a method for provision of a first trained generator function GF-1. The second example embodiment comprises all steps of the first example embodiment shown in FIG. 7, and can have all the embodiments and developments described with regard to the first example embodiment. The second example embodiment can in particular implement one or more of the data flow diagrams shown in FIG. 1 to FIG. 4.

The second example embodiment furthermore comprises a determination TDET-RDS-1-C of a first comparison real image dataset RDS-1-C of the examination volume VOL by application of a second trained generator function GF-2 to second input data via the training computing unit TCU of the training system TSYS, wherein the second input data comprises the differential image dataset DDS. Thus in particular the relationship $X^{(C)}_{fill,1}$=GF-2($Y_{DSA}$) applies for the first comparison real image dataset RDS-1-C.

The first comparison real image dataset RDS-1-C and the differential image dataset DDS in particular have an identical dimensionality. Furthermore, as regards each dimension, the extent of first comparison real image dataset RDS-1-C measured in pixels or voxels is identical to the extent of the differential image dataset DDS.

In this example embodiment the second trained generator function GF-2 is an artificial neural network or the second trained generator function GF-2 comprises an artificial neural network. Advantageously this artificial neural network comprises a residual block, a shortcut connection, a convolutional layer, a deconvolutional layer, a pooling layer and/or a spatial transformer layer. Furthermore, in this example embodiment for training of the second trained generator function GF-2 a cyclic consistency loss function CCL is minimized, through this a parameter the first trained generator function GF-2 is based in particular on this cyclic consistency loss function CCL. Furthermore in the training of the second trained generator function GF-2 an adversarial loss function AL can have been minimized.

A further step of the example embodiment shown is an adaptation TADJ-2 of the second trained generator function GF-2 based on a cyclic consistency loss function CCL, wherein the cyclic consistency loss function CCL is based on a comparison of the first real image dataset RDS-1 and the first comparison real image dataset RDS-1-C.

In this first example embodiment the second trained generator function GF-2 is adapted, in that one or more parameters of the second trained generator function GF-2 are adapted for optimization, in particular for minimization of a loss function $K^{(GF-2)}$.

The loss function $K^{(GF-2)}$ of the second trained generator function GF-2 here comprises a cyclic consistency loss function $K^{(GF-2)}_{CC}$. The amount $K^{(GF-2)}_{CC}$ of the cyclic consistency loss function is given by $K^{(GF-2)}_{CC}$=|$X_{Fill,1}$− $X^{(C)}_{fill,1}|_m$=|$X_{fill,1}$−GF-2(GF-1($X_{fill,1}$))$|_m$, wherein $|A|_m$ refers to the m-norm of A. In particular m=1 and m=2 can be selected. Since $X_{fill,1}$ and $X(C)_{fill,1}$ are image datasets in particular of the same dimensionality and the same extent, the norm can be calculated in pixels or in voxels in each case. A minimization of the cyclic consistency loss function leads to the second trained generator function GF-2 acting similarly to the inverse to the first trained generator function GF-1, and thus to a concatenation of the first trained generator function GF-1 and the second trained generator function GF-2 acting in a similar way to an identity mapping (and thus in a similar way to an autoencoder), and thus to the creation of image data being subject to fewer errors.

As an alternative or in addition to the steps of determination TDET-RDS-1-C of the first comparison real image dataset RDS-1-C and adaptation TADJ-2 of the second trained generator function GF-2, the second example embodiment can have the steps described below.

A further step of the second example embodiments is the receipt TREC-MDS-C of a comparison mask image dataset MDS-C of the examination volume via the training interface TIF of the training system TSYS.

The comparison mask image dataset MDS-C in this example embodiment has the same dimensionality and, as regards each dimension, the same extent measured in pixels or voxels as the first real image dataset RDS-1. Furthermore the mapping geometry used in the recording of the comparison mask image dataset MDS-C corresponds to the mapping geometry used in the recording of the first real image dataset RDS-1, in particular the examination volume has been recorded with regard to an identical projection direction. In particular the comparison mask image dataset MDS-C can correspond to the comparison differential dataset DDS-C, in particular in that the comparison differential dataset DDS-C has been determined as the difference between a further image dataset and the comparison mask image dataset MDS-C.

A further step of the second example embodiment is a determination TDET-MDS of a mask image dataset MDS of the examination volume VOL by application of the first trained generator function GF-1 to the first input data via the training computing unit TCU of the training system ISYS.

The mask image dataset MDS in this example embodiment has the same dimensionality and, in relation to each dimension, the same extent measured in pixels or voxels as the first real image dataset RDS-1.

In this example embodiment the differential image dataset DDS and the mask image dataset MDS are determined by the same application the first trained generator function GF-1. If M refers to the mask image dataset MDS, then for example (YDSA, M)=GF-1($X_{fill,1}$) applies. As an alternative the mask image dataset MDS can also be determined by a separate application of the first trained generator function GF-1.

The second example embodiment furthermore comprises a determination TDET-CV-M1 of a first mask classification value by application of a trained mask classifier function DF-M to the mask image dataset MDS, and a determination TDET-CV-M2 of a second mask classification value by application of a trained mask classifier function DF-M to the comparison mask image dataset MDS-C, via the training computing unit TCU of the training system TSYS in each case.

The first mask classification value here is a probability value r, this corresponds to the probability estimated by the mask classifier function DF-M that the mask image dataset MDS is a real image dataset. The second classification value here is a probability value $r^{(c)}$, this corresponds to the probability estimated by the mask classifier function DF-M that the comparison mask image dataset MDS-C is a real image dataset. Thus, in this example embodiment, r=DF-M(M)=DF-M(GF-1($X_{fill,1}$)) and $r^{(c)}$=DF-M($M^{(c)}$) apply, wherein $M^{(c)}$ refers to the comparison mask image dataset MDS-C. The calculation DF-M(GF-1( . . . )) is to be understood here in such a way that only the relevant values of the output values of the first trained generator function GF-1 will be used as input value for the trained mask classifier function DF-M.

The last step of the second example embodiment shown is the adaptation TADJ-3 of the first trained generator function GF-1 and/or of the trained mask classifier function DF-M based on the first mask classification value and/or the second mask classification value.

To this end, in this third example embodiment the loss function $K^{(DF-M)}$ of the trained mask classifier function DF-M is given by an adversarial loss function $K^{(DF-M)}_A$=−BCE(DF-M($Y^{(c)}$), 1)−BCE(DF-M(Y), 0)=−BCE($r^{(c)}$, 1)−BCE(r, 0). In particular the adversarial loss function $K^{(DF-M)}_A$ is thus given by $K^{(DF-1)}_A$=−log(DF-1($Y^{(c)}$))−log(1−DF-1(Y))=−log($r^{(c)}$)−log(1−r). In a minimization of this loss function the trained mask classifier function DF-M is embodied to distinguish as well as possible between real image data (corresponding to the comparison mask image datasets MDS-C) and synthetic image data (corresponding to the mask image datasets MDS) created by the first trained generator function GF-1.

An additional adversarial loss function $K^{(GF-1)}_{MA}$=−BCE(DF-M(Y), 1)=−log(r) can in particular likewise be used for the loss function $K^{(GF-1)}$ of the first trained generator function GF-1. In a minimization of this loss function the first trained generator function GF-1 is embodied to create such mask image datasets MDS as will be classified incorrectly by the trained mask classifier function DF-M as real image data.

Figure 9:
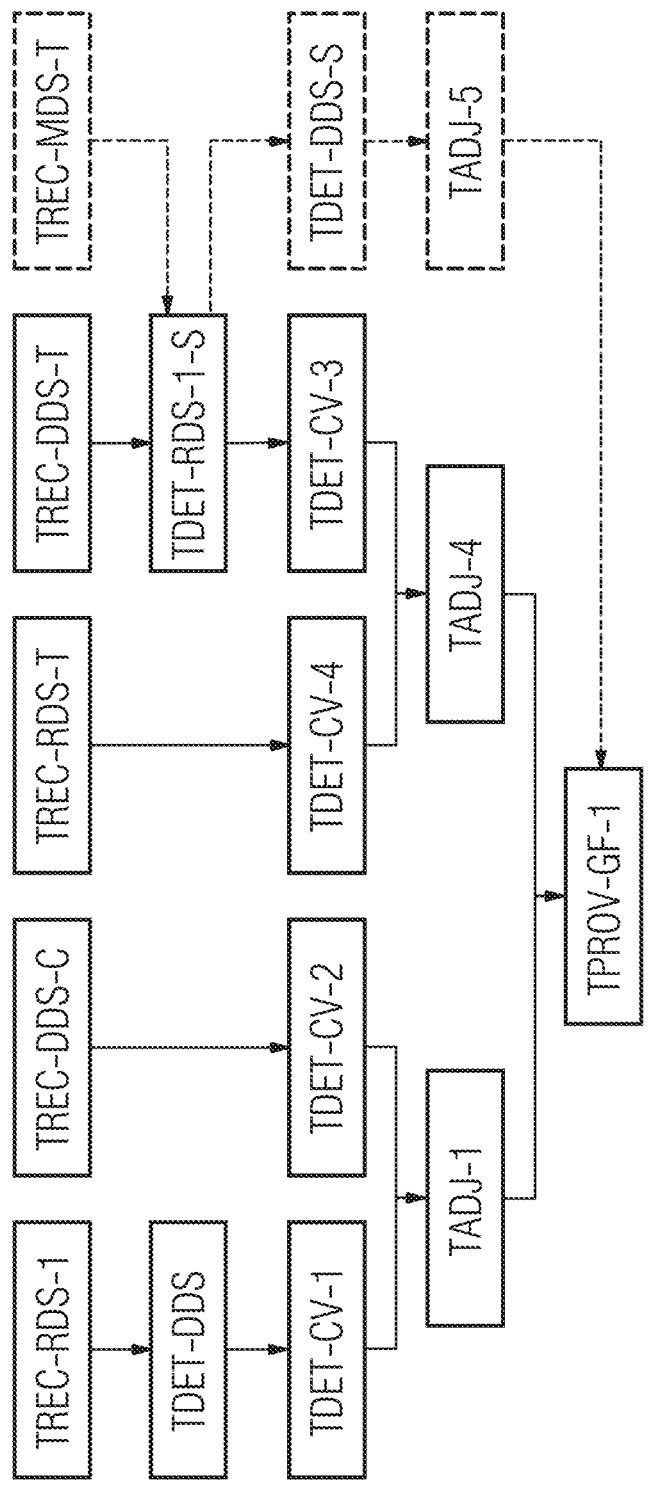
FIG. 9 shows a third example embodiment of a method for provision of a first trained generator function.

FIG. 9 shows a third example embodiment of a method for provision of a first trained generator function GF-1. The third example embodiment comprises all steps of the first example embodiment shown in FIG. 7, and can have all embodiments and developments described with regard to the first example embodiment. The third example embodiment can in particular implement one or more of the data flow diagrams shown in FIG. 1 to FIG. 4.

A further step of the third example embodiment is the receipt TREC-DDS-T of a training differential image dataset DDS-T of the examination volume VOL, as well as the receipt TREC-RDS-T of a training real image dataset RDS-T of the examination volume VOL, in particular via the training interface TIF of the training system TSYS. The training differential image dataset DDS-T and the training real image dataset RDS-T can in particular have the same dimensionality and, as regards each dimension, the same extent as the first real image dataset RDS-1 measured in pixels or voxels.

A further step of the third example embodiment shown is the determination TDET-RDS-1-S of a first synthetic real image dataset RDS-1-S by application of the second trained generator function GF-2 to second training input data, wherein the second training input data comprises the training differential image dataset DDT-T. The determination TDET-RDS-1-S of the first synthetic real image dataset RDS-1-S is undertaken in particular via the training computing unit TCU of the training system TSYS. If $Y^{(T)}_{DSA}$ refers to the training differential image dataset DDS-T and if $X^{(S)}_{fill,1}$ refers to the first synthetic real image dataset RDS-1-S, then $X^{(S)}_{fill,1}$=GF-2($Y^{(T)}_{DSA}$) applies here.

Optionally, in this third example embodiment, there can be a receipt TREC-MDS-T of a training mask image dataset MDS-T of the examination volume VOL, in particular via the training interface TIF of the training system TSYS, wherein the second training input data then furthermore comprises the training mask image dataset MDS-T. Then in particular $X^{(S)}_{fill,1}=\text{GF-2}(Y^{(T)}_{DSA}, M^{(T)})$ applies here.

Further steps of the third example embodiment are the determination TDET-CV-3 of a third classification value by application of a second trained classifier function DF-2 to the synthetic real image dataset RDS-1-S, as well as the determination TDET-CV-4 of a fourth classification value by the second trained classifier function DF-2 on the training real image dataset RDS-T, via the training computing unit TCU of the training system TSYS in each case.

The third classification value here is a probability value q, this corresponds to the probability that the first synthetic real image dataset RDS-1-S estimated by the second trained classifier function DF-2 is a real image dataset. The fourth classification value here is a probability value $q^{(c)}$, this corresponds to the probability that the training real image dataset RDS-T is a real image dataset estimated by the second trained classifier function DF-2. Thus, in this example embodiment, $q=\text{DF-2}(X^{(S)}_{fill,1})=\text{DF-2}(\text{GF-2}(Y^{(T)}_{DSA}))$ and $p^{(c)}=\text{DF-2}(X^{(T)}_{fill})$, wherein $X^{(T)}_{fill}$ refers to the training real image dataset RDS-T.

A further step of the example embodiment shown is an adaptation TADJ-4 of the second trained generator function GF-2 and/or of the second trained classifier function DF-2 based on the third classification value and/or the fourth classification value, in particular via the training computing unit TCU of the training system TSYS.

In this first example embodiment the second trained generator function GF-2 is adapted, in that one or more parameters of the second trained generator function GF-2 are adapted for optimization, in particular for minimization, of a loss function $K^{(GF-2)}$. Furthermore the second trained classifier function DF-2 is adapted, in that one or more parameters of the second trained classifier function DF-2 are adapted for optimization, in particular for minimization, of a loss function $K^{(DF-2)}$.

The loss function $K^{(DF-2)}$ here comprises an adversarial loss function $K^{(DF-2)}_A=-\text{BCE}(\text{DF-2}(X^{(T)}_{fill}), 1)-\text{BCE}(\text{DF-2}(X^{(S)}_{fill,1}), 0)=-\text{BCE}(q^{(c)}, 1)-\text{BCE}(q, 0)$. Thus in particular the adversarial loss function $K^{(DF-2)}_A$ is given by $K^{(DF-2)}_A=-\log(\text{DF-1}(X^{(T)}_{fill}))-\log(1-\text{DF-1}(X^{(S)}_{fill,1}))=-\log(q^{(c)})-\log(1-q)$. In a minimization of this loss function the second trained classifier function DF-2 is embodied to distinguish as well as possible between real image data (corresponding to the training real image datasets RDS-T) and synthetic image data (corresponding to the first synthetic real image dataset RDS-1-S) created by the second trained generator function GF-2.

An adversarial loss function $K^{(GF-2)}_A=-\text{BCE}(\text{DF-2}(X^{(S)}_{fill,1}), 1)=-\log(q)$ can in particular likewise be used in the loss function $K^{(GF-2)}$ of the second trained generator function GF-2. In a minimization of this loss function the second trained generator function GF-2 is embodied to create such first synthetic real image datasets RDS-1-S as are incorrectly classified by the second trained classifier function DF-2 as real image data.

In this example embodiment the second trained classifier function DF-2 is an artificial neural network or the second trained classifier function DF-2 comprises an artificial neural network. Advantageously this artificial neural network comprises a residual block, a shortcut connection, a convolutional layer, a deconvolutional layer, a pooling layer and/or spatial transformer layer. Furthermore in training the second trained classifier function DF-2 an adversarial loss function AL can have been minimized.

A further optional step of the third example embodiment is the determination TDET-DDS-S of a synthetic differential image dataset DDS-S of the examination volume VOL by application of the first trained generator function GF-1 to first training input data, wherein the first training input data comprises the first synthetic real image dataset RDS-1-S, in particular via the training computing unit TCU of the training system TSYS.

The synthetic differential image dataset DDS-S can in particular have the same dimensionality and, as regards each dimension, the same extent of the first real image dataset RDS-1 measured in pixels or voxels. If $Y^{(S)}_{DSA}$ refers to the synthetic differential image dataset DDS-S, then thus $Y^{(S)}_{DSA}=\text{GF-1}(X^{(S)}_{fill,1})$ applies.

A further optional step of the example embodiment shown is the adaptation TADJ-5 of the first trained generator function GF-1 based on a cyclic consistency loss function CCL, wherein the cyclic consistency loss function CCL is based on a comparison of the training differential image dataset DDS-T and the synthetic differential image dataset DDS-S.

In this third example embodiment the first trained generator function GF-1 is adapted, in that one or more parameters of the first trained generator function GF-1 are adapted for optimization, in particular for minimization of a loss function $K^{(GF-1)}$.

The loss function $K^{(GF-1)}$ of the first trained generator function GF-1 here comprises a cyclic consistency loss function $K^{(GF-1)}_{CC}$. The amount $K^{(GF-1)}_{CC}$ of the cyclic consistency loss function is given by $K^{(GF-1)}_{CC}=|Y^{(T)}_{DSA}-Y^{(S)}_{DSA}|_m=|Y^{(T)}_{DSA}-\text{GF-1}(\text{GF-2}(Y^{(T)}_{DSA}))|_m$, wherein $|A|_m$ refers to the m-norm of A. In particular m=1 and m=2 can be selected. Since $Y^{(T)}_{DSA}$ and $Y^{(S)}_{DSA}$ are image datasets in particular of the same dimensionality and the same extent, the norm can be calculated in pixels or in voxels in each case. A minimization of the cyclic consistency loss function leads to the first trained generator function GF-1 acting in a similar way to the inverse to the second trained generator function GF-2, and thus a concatenation of the second trained generator function GF-2 and the first trained generator function GF-1 acting in a similar way to an identity mapping (and thus in a similar way to an autoencoder), and thus to the creation of image data being subject to fewer errors.

Figure 10:
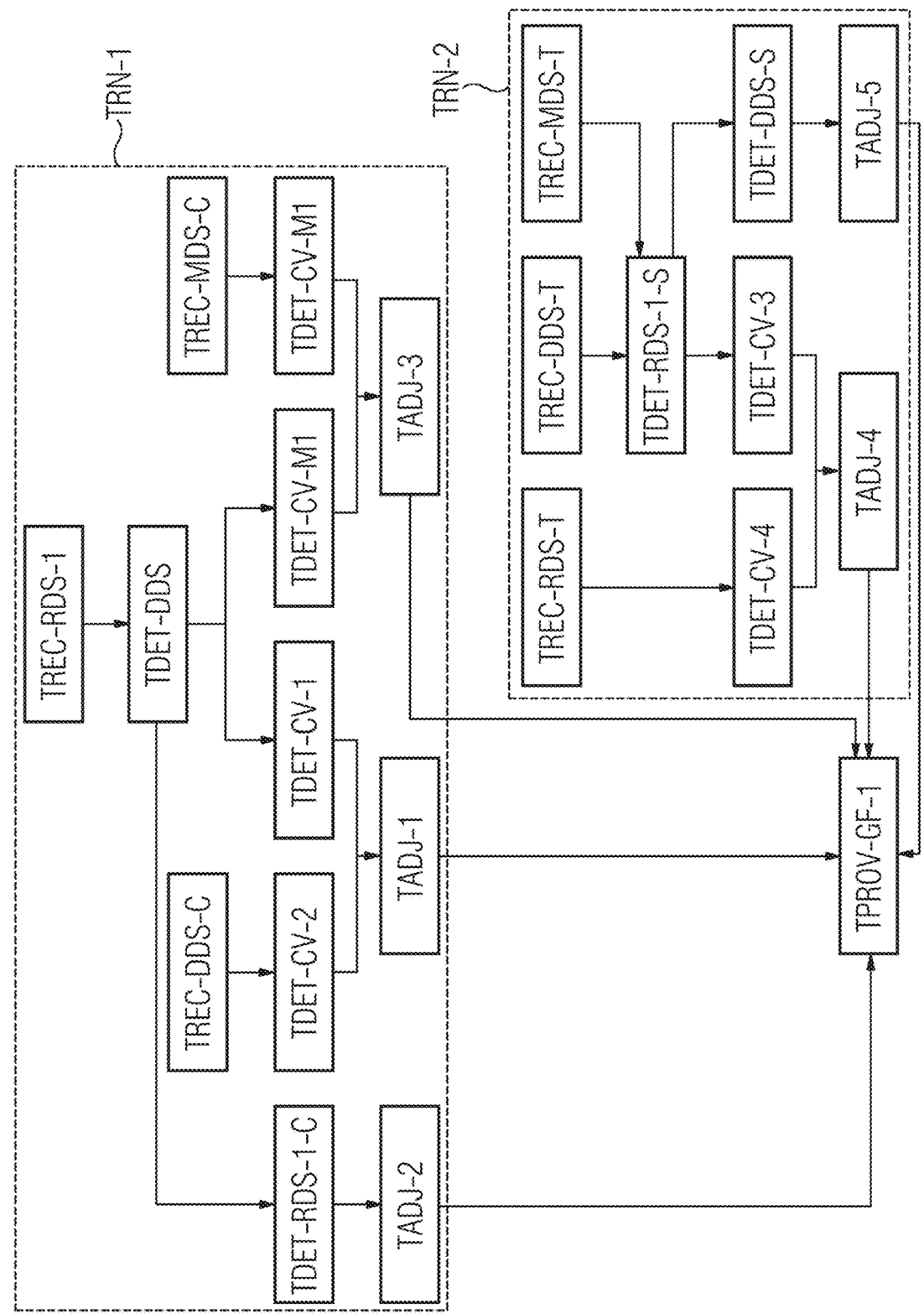
FIG. 10 shows a fourth example embodiment of a method for provision of a first trained generator function.

FIG. 10 shows a fourth example embodiment of a method for provision of a first trained generator function GF-1. The fourth example embodiment combines the elements of the first to third example embodiments shown in FIG. 7 to FIG. 9. In particular the steps can be divided into a first training TRN-1 and a second training TRN-2, wherein the generator functions GF-1, GF-2 are each trained in pairs with the classifier functions DF-1, DF-2, DF-M. The fourth example embodiment can in particular implement one or more of the data flow diagrams shown in FIG. 1 to FIG. 4.

The loss functions of the generator functions GF-1, GF-2 and of the classifier function DF-1, DF-2, DF-M here can comprise an adversarial loss function AL as a component. Furthermore the loss functions of the generator functions GF-1, GF-2 can comprise a cyclic consistency loss function CCL. For example the respective loss functions can be given by $$K^{(GF-1)}=K^{(GF-1)}_A+K^{(GF-1)}_{MA}+K^{(GF-1)}_{CC}$$

$$K^{(GF-2)}=K^{(GF-2)}_A+K^{(GF-2)}_{CC}$$

$$K^{(DF-1)} = K^{(DF-1)}{}_A$$

$$K^{(DF-2)} = K^{(DF-2)}{}_A$$

$$K^{(DF-M)} = K^{(DF-M)}{}_A$$

Figure 11:
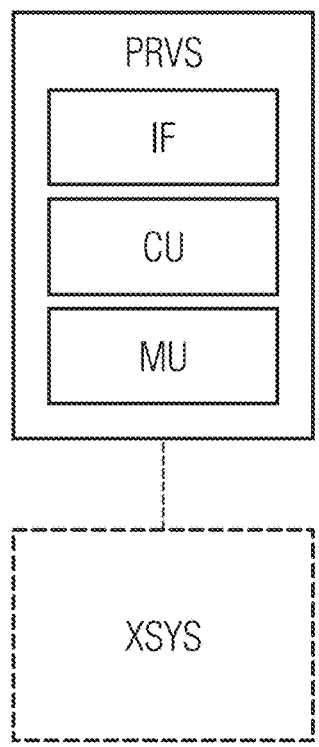
FIG. 11 shows a provision system.
Figure 12:
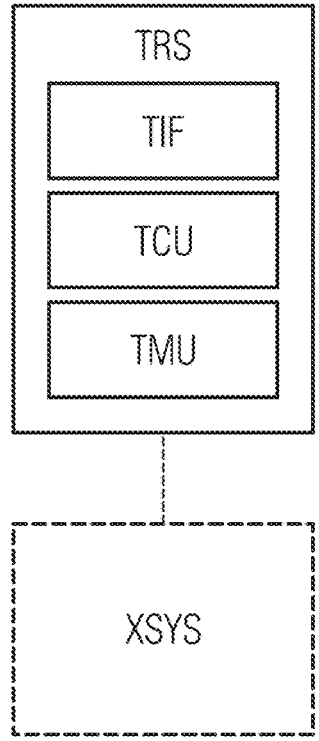
FIG. 12 shows a training system.

FIG. 11 shows a provision system PRVS, FIG. 12 shows a training system TSYS. The provision system PRVS shown is embodied to carry out an inventive method for provision of a differential image dataset DDS. The training system TSYS shown is embodied to carry out an inventive method for provision of a first trained generator function GF-1 and/or of a first trained classifier function DF-1. The provision system PRVS comprises an interface IF, a computing unit CU and a memory unit MU, the training system TSYS comprises a training interface TIF, a training computing unit TCU and training memory unit TMU.

The provision system PRVS and/or the training system TSYS can in particular involve a computer, a microcontroller or an integrated circuit. As an alternative the provision system PRVS and/or the training system TSYS can involve a real or virtual network of computers (a real network is referred to as a cluster, a virtual network is referred to as a cloud). The provision system PRVS and/or the training system TSYS can also be embodied as a virtual system, which is executed on a real computer or on a real or virtual network of computers (referred to as virtualization).

An interface IF and/or a training interface TIF can involve a hardware or software interface (for example PCI bus, USB or Firewire). A computing unit CU and/or a training computing unit TCU can have hardware elements or software elements, for example a microprocessor or what is known as an FPGA (Field Programmable Gate Array). A memory unit MU and/or a training memory unit TMU can be realized as non-permanent working storage (Random Access Memory, abbreviated to RAM) or as permanent mass storage (hard disk, USB stick, SD card, solid state disk).

The interface IF and/or the training interface TIF can in particular comprise a number of sub-interfaces, which carry out different steps of the respective methods. In other words the interface IF and/or the training interface TIF can also be expressed as a plurality of interfaces IF or a plurality of training interfaces TIF. The computing unit CU and/or the training computing unit TCU can in particular comprise a number of sub-computing units, which carry out different steps of the respective methods. In other words the computing unit CU and/or the training computing unit TCU can also be expressed as a plurality of computing units CU or a plurality of training computing units TCU.

FIG. 13 shows an x-ray facility XSYS connected to a provision system PRVS. In the example embodiment shown the x-ray facility XSYS involves a C-arm x-ray system XSYS. The C-arm x-ray system XSYS comprises an x-ray source XSYS.SRC for emitting x-rays. Furthermore the C-arm x-ray system XSYS comprise an x-ray detector XSYS.DTC for receiving x-rays. The x-ray source XSYS.SRC and also the x-ray detector XSYS.DTC are attached to the two different ends of the C-arm XSYS.ARM. The C-arm XSYS.ARM of the C-arm x-ray system XSYS is attached to a stand XSYS.STC. The stand XSYS.STC comprises drive elements that are designed to change the position of the C-arm XSYS.ARM. In particular the C-arm XSYS.ARM can be rotated about two different axes. The C-arm x-ray system furthermore comprises a control and evaluation unit XSYS.CTRL and also a patient support facility XSYS.PAT on which a patient PAT can be supported. Via the control and evaluation unit XSYS.CTRL the position of the C-arm XSYS.ARM can be adjusted, the C-arm XSYS.ARM rotated about the examination volume VOL and x-ray image datasets of the examination volume VOL recorded. As an alternative to the example embodiment shown, it is also possible for the provision system PRVS to be embodied as part of the control and evaluation unit XSYS.CTRL.

Where this has not happened explicitly, but is sensible and in the spirit of the invention, individual example embodiments, individual of their sub-aspects or features can be combined with one another or exchanged, without departing from the framework of the present invention. Advantages of the invention described with regard to one example embodiment also apply, where they can be transferred, to other example embodiments, without this being explicit stated.

Although the invention has been illustrated and described in greater detail with reference to the referred example embodiments, the invention is not restricted thereby. Other variations and combinations can be derived herefrom by the person skilled in the art without departing from the essential concept of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for provision of a first trained generator function, the computer-implemented method comprising:
   receiving a first real image dataset of an examination volume;
   receiving a comparison differential image dataset of the examination volume;
   determining a differential image dataset of the examination volume by application of the first trained generator function to first input data, the first input data including the first real image dataset;

determining a first classification value by application of a first trained classifier function to the differential image dataset;

determining a second classification value by application of the first trained classifier function to the comparison differential image dataset;

adapting at least one of the first trained generator function or the first trained classifier function based on at least one of the first classification value or the second classification value; and provisioning the first trained generator function.

2. The method of claim 1, further comprising:

determining a first comparison real image dataset of the examination volume by application of a second trained generator function to second input data, the second input data including the differential image dataset; and adapting the second trained generator function based on a cyclic consistency loss function, the cyclic consistency loss function being based on a comparison of the first real image dataset and the first comparison real image dataset.

3. The method of claim 1, further comprising:

receiving a comparison mask image dataset of the examination volume;

determining a mask image dataset of the examination volume by application of the first trained generator function to the first input data;

determining a first mask classification value by application of a trained mask classifier function to the mask image dataset;

determining a second mask classification value by application of the trained mask classifier function to the comparison mask image dataset; and adapting at least one of the first trained generator function or the trained mask classifier function based on at least one of the first mask classification value or the second mask classification value.

4. The method of claim 1, further comprising:

receiving a training differential image dataset of the examination volume;

receiving a training real image dataset of the examination volume;

determining a first synthetic real image dataset by application of a second trained generator function to second training input data, the second training input data including the training differential image dataset;

determining a third classification value by application of a second trained classifier function to the first synthetic real image dataset;

determining a fourth classification value by application of the second trained classifier function to the training real image dataset; and adapting at least one of the second trained generator function or the second trained classifier function based on at least one of the third classification value or the fourth classification value.

5. The method as claimed in claim 4, further comprising:

determining a synthetic differential image dataset of the examination volume by application of the first trained generator function to first training input data, the first training input data including the first synthetic real image dataset; and adapting the first trained generator function based on a cyclic consistency loss function, the cyclic consistency loss function being based on a comparison of the training differential image dataset and the synthetic differential image dataset.

6. The method of claim 4, further comprising:

receiving a training mask image dataset of the examination volume, the second training input data further including the training mask image dataset.

7. The method of claim 6, wherein, upon applying the first trained generator function to first training input data, a synthetic mask image dataset is determined, and wherein a cyclic consistency loss function is based on a comparison of the training mask image dataset and the synthetic mask image dataset.

8. The method of claim 2, further comprising:

receiving a comparison mask image dataset of the examination volume;

determining a mask image dataset of the examination volume by application of the first trained generator function to the first input data;

determining a first mask classification value by application of a trained mask classifier function to the mask image dataset;

determining a second mask classification value by application of the trained mask classifier function to the comparison mask image dataset; and adapting at least one of the first trained generator function or the trained mask classifier function based on at least one of the first mask classification value or the second mask classification value.

9. The method of claim 2, further comprising:

receiving a training differential image dataset of the examination volume;

receiving a training real image dataset of the examination volume;

determining a first synthetic real image dataset by application of the second trained generator function to second training input data, the second training input data including the training differential image dataset;

determining a third classification value by application of a second trained classifier function to the first synthetic real image dataset;

determining a fourth classification value by application of the second trained classifier function to the training real image dataset; and adapting at least one of the second trained generator function or the second trained classifier function based on at least one of the third classification value or the fourth classification value.

10. A computer-implemented method for provision of a differential image dataset of an examination volume, the computer-implemented method comprising:

receiving a first real image dataset of the examination volume, the examination volume including a vessel, the first real image dataset mapping the examination volume including contrast medium;

determining the differential image dataset of the examination volume by application of a first trained generator function to input data, the input data including the first real image dataset, and a parameter of the first trained generator function being based on a generative adversarial (GA) algorithm; and provisioning the differential image dataset, wherein the first trained generator function has been provided by the method of claim 1.

11. A non-transitory computer-readable storage medium storing program sections, readable and executable by a provision system, for carrying out the method of claim 1 when the program sections are executed by the provision system.

12. A provision system for provision of a differential image dataset of an examination volume, the provision system comprising:
   an interface embodied to receive of a first real image dataset of the examination volume, the examination volume including a vessel and the first real image dataset mapping the examination volume including contrast medium; and
   a computing unit, embodied to determine the differential image dataset of the examination volume by application of a first trained generator function to input data, the input data including the first real image dataset and a parameter of the first trained generator function being based on a generative adversarial (GA) algorithm,
   wherein the interface is further embodied to provision the differential image dataset.

13. A computer-implemented method for provision of a differential image dataset of an examination volume, the computer-implemented method comprising:
   receiving a first real image dataset of the examination volume, the examination volume including a vessel, and the first real image dataset mapping the examination volume including contrast medium;
   determining the differential image dataset of the examination volume by application of a first trained generator function to input data, the input data including the first real image dataset, and a parameter of the first trained generator function being based on a generative adversarial (GA) algorithm; and
   provisioning the differential image dataset.

14. The method of claim 13, wherein the first real image dataset includes a first noise level, wherein the differential image dataset includes a second noise level, and wherein the first noise level is higher than the second noise level.

15. The method of claim 13, wherein the first real image dataset is an x-ray image dataset.

16. The method of claim 13, further comprising:
   determining a mask image dataset of the examination volume by application of the first trained generator function to the input data, wherein the mask image dataset maps the examination volume without contrast medium.

17. The method of claim 13, further comprising:
   receiving a second real image dataset of the examination volume, wherein the first real image dataset maps the examination volume at a first point in time, wherein the second real image dataset maps the examination volume at a second point in time, and wherein the input data further comprises the second real image dataset.

18. The method of claim 13, wherein there is patch-wise application of the first trained generator function to image datasets contained in the input data.

19. The method of claim 13, wherein the parameter of the first trained generator function is based on a cyclic consistency loss function.

20. A non-transitory computer-readable storage medium storing program sections, readable and executable by a provision system, for carrying out the method of claim 13 when the program sections are executed by the provision system.

* * * * *